(12) United States Patent
Krieg et al.

(10) Patent No.: US 11,767,523 B2
(45) Date of Patent: Sep. 26, 2023

(54) ACRYLAMIDE COPOLYMERIZATION FOR SEQUESTRATION AND PRODUCTION OF SINGLE-STRANDED NUCLEIC ACID

(71) Applicant: Dana-Farber Cancer Institute, Inc., Boston, MA (US)

(72) Inventors: Elisha Krieg, Dresden (DE); William M. Shih, Cambridge, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1126 days.

(21) Appl. No.: 16/332,674

(22) PCT Filed: Sep. 11, 2017

(86) PCT No.: PCT/US2017/050929
§ 371 (c)(1),
(2) Date: Mar. 12, 2019

(87) PCT Pub. No.: WO2018/049315
PCT Pub. Date: Mar. 15, 2018

(65) Prior Publication Data
US 2020/0190505 A1   Jun. 18, 2020

Related U.S. Application Data

(60) Provisional application No. 62/393,600, filed on Sep. 12, 2016.

(51) Int. Cl.
*C12N 15/10* (2006.01)
*C08F 220/56* (2006.01)
*C12Q 1/6806* (2018.01)

(52) U.S. Cl.
CPC ........ *C12N 15/1006* (2013.01); *C08F 220/56* (2013.01); *C12N 15/1017* (2013.01); *C12Q 1/6806* (2013.01); *C08J 2333/26* (2013.01); *C12N 2310/00* (2013.01); *C12N 2330/30* (2013.01); *C12Q 2523/305* (2013.01); *C12Q 2523/32* (2013.01); *C12Q 2525/204* (2013.01)

(58) Field of Classification Search
CPC ............ C12N 15/1006; C12N 15/1017; C12Q 1/6806; C08F 220/56; C08J 2333/26
See application file for complete search history.

(56) References Cited

U.S. PATENT DOCUMENTS

| 9,085,802 B2 | 7/2015 | Liu et al. |
| 2005/0009101 A1 | 1/2005 | Blackburn |

(Continued)

FOREIGN PATENT DOCUMENTS

| WO | WO 1996/040901 A1 | 12/1996 |
| WO | WO 2015/122845 A1 | 8/2015 |
| WO | WO 2016/114970 A1 | 7/2016 |

OTHER PUBLICATIONS

Xiao et al. "Gel Immobilization of Acrylamide-Modified Single-Stranded DNA Template for Pyrosequencing". Electrophoresis 2007, 28, 1903-1912 (Year: 2007).*

(Continued)

*Primary Examiner* — Jezia Riley
(74) *Attorney, Agent, or Firm* — Wolf, Greenfield & Sacks, P.C.

(57) ABSTRACT

Provided herein, in some embodiments, are methods, compositions and kits for large-scale production of long single-stranded DNA in solution.

22 Claims, 13 Drawing Sheets

Specification includes a Sequence Listing.

(56) References Cited

U.S. PATENT DOCUMENTS

| | | |
|---|---|---|
| 2009/0277791 A1 | 11/2009 | Vu et al. |
| 2015/0299366 A1 | 10/2015 | Zhang et al. |
| 2021/0032683 A1 | 2/2021 | Krieg et al. |

OTHER PUBLICATIONS

Buenemann et al., Synthesis and properties of acrylamide-substituted base pair specific dyes for deoxyribonucleic acid template mediated synthesis of dye polymers. Biochemistry. May 12, 1981;20(10):2864-74.

Chan et al., Capillary electrophoresis for capture and concentrating of target nucleic acids by affinity gels modified to contain single-stranded nucleic acid probes. Anal Chim Acta. Sep. 18, 2006;578(1):31-42. Epub May 27, 2006.

Li et al., Functional nucleic acid-based hydrogels for bioanalytical and biomedical applications. Chem Soc Rev. Mar. 7, 2016;45(5):1410-31. doi: 10.1039/c5cs00586h.

Paegel et al., Microchip bioprocessor for integrated anovolume sample purification and DNA sequencing. Anal Chem. Oct. 1, 2002;74(19):5092-8.

Tang et al., Polymerizing immobilization of acrylamide-modified nucleic acids and its application. Biosens Bioelectron. Mar. 15, 2009;24(7):1817-24. doi:10.1016/j.bios.2008.09.018. Epub Sep. 27, 2008.

Beaucage et al., "Deoxynucleoside phosphoramidites—A new class of key intermediates for deoxypolynucleotide synthesis." Tetrahedron Lett. 1981; 22:1859-62.

Beliveau et al., "OligoMiner provides a rapid, flexible environment for the design of genome-scale oligonucleotide in situ hybridization probes." Proc Natl Acad Sci U S A. Mar. 6, 2018;115(10):E2183-E2192. doi: 10.1073/pnas.1714530115. Epub Feb. 20, 2018.

Beliveau et al., "Versatile design and synthesis platform for visualizing genomes with Oligopaint FISH probes." Proc Natl Acad Sci U S A. Dec. 26, 2012; 109(52):21301-6. doi: 10.1073/pnas.1213818110. Epub Dec. 11, 2012.

Chandra et al., "DNA-catalyzed sequence-specific hydrolysis of DNA." Nat Chem Biol. Oct. 2009; 5(10):718-20. doi: 10.1038/nchembio.201. Epub Aug. 16, 2009.

Damase et al., "Purification of single-stranded DNA by co-polymerization with acrylamide and electrophoresis." BioTechniques. Jun. 1, 2017; 62(6):275-282; DOI:10.2144/000114557.

Davis et al., "Two Distinct Pathways Support Gene Correction by Single-Stranded Donors at DNA Nicks." Cell Rep. Nov. 8, 2016;; 17(7):1872-1881. doi: 10.1016/j.celrep.2016.10.049.

Forster et al., "Hydrophobically Modified Polyacrylamide Block Copolymers for 65 Fast, High-Resolution DNA Sequencing in Microfluidic Chips." Electrophoresis. Dec. 2008; 29(23):4669-4676.

Gu et al., "Small, highly active DNAs that hydrolyze DNA." J Am Chem Soc. Jun. 19, 2013; 135(24):9121-9. doi: 10.1021/ja403585e. Epub Jun. 6, 2013.

Gyllensten et al., "Generation of single-stranded DNA by the polymerase chain reaction and its application to direct sequencing of the HLA-DQA locus." Proc Natl Acad Sci U S A. Oct. 1988; 85(20):7652-6.

Kajua et al., "Efficient preparation of single-stranded DNA for in vitro selection." Mol Biotechnol. Jun. 1997; 7(3):333-5.

Kenney et al., "Mutation typing using electrophoresis and gel-immobilized Acrydite probes." Biotechniques. Sep. 1998; 25(3):516-21.

Kick et al., "Efficient Production of Single-Stranded Phage DNA as Scaffolds for DNA Origami." Nano Lett. Jul. 8, 2015; 15(7):4672-6. doi: 10.1021/acs.nanolett.5b01461. Epub Jun. 3, 2015.

Kishi et al., "Programmable autonomous synthesis of single-stranded DNA." Nat Chem. Feb. 2018; 10(2):155-164. doi: 10.1038/nchem.2872. Epub Nov. 6, 2017.

Kosuri et al., "Large-scale de novo DNA synthesis: technologies and applications." Nat Methods. May 2014; 11(5):499-507. doi: 10.1038/nmeth.2918.

Krieg et al., "A recyclable supramolecular membrane for size-selective separation of nanoparticles." Nat Nanotechnol. Mar. 2011; 6(3):141-6. doi: 10.1038/nnano.2010.274. Epub Jan. 23, 2011.

Krieg et al., "Selective Nascent Polymer Catch- and-Release Enables Scalable Isolation of Multi-Kilobase Single-Stranded DNA." Angew. Chem. Int. Ed. 2018; 57:714-18.

McHugh et al., "Novel reagents for chemical cleavage at abasic sites and UV photoproducts in DNA." Nucleic Acids Res. May 25, 1995; 23(10):1664-70.

Minev et al., "Rapid and scalable in vitro production of single-stranded DNA." (accessed https://doi.org/10.1101/558429).

Palluck et al., De novo DNA synthesis using polymerase-nucleotide conjugates. Nat Biotechnol. Aug. 2018; 36(7):645-650. doi: 10.1038/nbt.4173. Epub Jun. 18, 2018.

Ponnuswamy et al., "Oligolysine-based coating protects DNA nanostructures from low-salt denaturation and nuclease degradation." Nat Commun. May 31, 2017; 8:15654. doi: 10.1038/ncomms15654.

Pound et al., "Polymerase chain reaction based scaffold preparation for the production of thin, branched DNA origami nanostructures of arbitrary sizes." Nano Lett. Dec. 2009; 9(12):4302-5. doi: 10.1021/nl902535q.

Praetorius et al., "Biotechnological mass production of DNA origami." Nature. Dec. 6, 2017; 552(7683):84-87. doi: 10.1038/nature24650.

Rehman et al., "Immobilization of acrylamide-modified oligonucleotides by co-polymerization." Nucleic Acids Res. Jan. 15, 1999; 27(2):649-55.

Richardson et al., "Enhancing homology-directed genome editing by catalytically active and inactive CRISPR-Cas9 using asymmetric donor DNA." Nat Biotechnol. Mar. 2016; 34(3):339-44. doi: 10.1038/nbt.3481. Epub Jan. 20, 2016.

Roth et al., "Reprogramming human T cell function and specificity with non-viral genome targeting." Nature. Jul. 2018; 559(7714):405-409. doi: 10.1038/s41586-018-0326-5. Epub Jul. 11, 2018.

Schindelin et al., "Fiji: an open-source platform for biological-image analysis." Nat Methods. Jun. 28, 2012; 9(7):676-82. doi: 10.1038/nmeth.2019.

Schmidt et al., "Scalable amplification of strand subsets from chip-synthesized oligonucleotide libraries." Nat Commun. Nov. 16, 2015;6:8634. doi: 10.1038/ncomms9634.

Seeman, N.C., "An overview of structural DNA nanotechnology." Mol Biotechnol. Nov. 2007;37(3):246-57. Epub Jul. 12, 2007.

Svobodová et al., "Comparison of different methods for generation of single-stranded DNA for SELEX processes." Anal Bioanal Chem. Aug. 2012; 404(3):835-42. doi: 10.1007/s00216-012-6183-4. Epub Jun. 26, 2012.

Vasiliskov et al., "Fabrication of microarray of gel-immobilized compounds on a chip by copolymerization." Biotechniques. Sep. 1999;27(3):592-4, 596-8, 600 passim.

Veneziano et al., "Designer nanoscale DNA assemblies programmed from the top down." Science. Jun. 24, 2016; 352(6293):1534. doi: 10.1126/science.aaf4388. Epub May 26, 2016.

Veneziano et al., "In vitro synthesis of gene-length single-stranded DNA." Sci Rep. Apr. 25, 2018; 8(1):6548. doi: 10.1038/s41598-018-24677-5.

Walker et al., "Isothermal in vitro amplification of DNA by a restriction enzyme/DNA polymerase system." Proc Natl Acad Sci U S A. Jan. 1, 1992; 89(1):392-6.

Wei et al., "Capture and release of protein by a reversible DNA-induced sol-gel transition system." Angew Chem Int Ed Engl. 2008; 47(2):331-3.

Xiao et al., "Gel Immobilization of Acrylamide-Modified Single-Stranded DNA Template for Pyrosequencing. Advances in Clinical Practice in Pyrosequencing, Chapter 6." Springer Protocols Handbooks. Feb. 5, 2016.

Xiong et al., "Responsive DNA-based hydrogels and their applications." Macromol Rapid Commun. Aug. 2013;34(16):1271-83. doi: 10.1002/marc.201300411. Epub Jul. 16, 2013.

(56) References Cited

OTHER PUBLICATIONS

Amir et al., Universal computing by DNA origami robots in a living animal. Nat Nanotechnol. May 2014;9(5):353-357. doi: 10.1038/nnano.2014.58. Epub Apr. 6, 2014.

Andersen et al., Self-assembly of a nanoscale DNA box with a controllable lid. Nature. May 7, 2009;459(7243):73-6. doi: 10.1038/nature07971.

Bowman et al., Rapid production of single-stranded sequencing template from amplified DNA using magnetic beads. Methods Enzymol. 1993;224:399-406. doi: 10.1016/0076-6879(93)24030-x.

Chen et al., Self-Assembly of Large DNA Origami with Custom-Designed Scaffolds. ACS Appl Mater Interfaces. Jul. 25, 2018;10(29):24344-24348. doi: 10.1021/acsami.8b09222. Epub Jul. 12, 2018.

Dave et al., Regenerable DNA-functionalized hydrogels for ultrasensitive, instrument-free mercury(II) detection and removal in water. J Am Chem Soc. Sep. 15, 2010;132(36):12668-73. doi: 10.1021/ja106098j.

Douglas et al., A logic-gated nanorobot for targeted transport of molecular payloads. Science. Feb. 17, 2012;335(6070):831-4. doi: 10.1126/science.1214081.

Douglas et al., DNA-nanotube-induced alignment of membrane proteins for NMR structure determination. Proc Natl Acad Sci U S A. Apr. 17, 2007;104(16):6644-8. doi: 10.1073/pnas.0700930104. Epub Apr. 2, 2007.

Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.

Douglas et al., Self-assembly of DNA into nanoscale three-dimensional shapes. Nature. May 21, 2009;459(7245):414-8. doi: 10.1038/nature08016.

Fire et al., Rolling replication of short DNA circles. Proc Natl Acad Sci U S A. May 9, 1995;92(10):4641-5. doi: 10.1073/pnas.92.10.4641.

Hannon et al., Synthesis of PCR-derived, single-stranded DNA probes suitable for in situ hybridization. Anal Biochem. Aug. 1, 1993;212(2):421-7. doi: 10.1006/abio.1993.1350.

He et al., Aptamer based reversible DNA induced hydrogel system for molecular recognition and separation. Chem Commun (Camb). Sep. 14, 2010;46(34):6308-10. doi: 10.1039/c0cc01392g. Epub Jul. 30, 2010.

Hermanson, G. T. Bioconjugate Techniques, Third Edition. (Academic Press, 2013).

Joneja et al., Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.

Kishi et al., SABER enables highly multiplexed and amplified detection of DNA and RNA in cells and tissues. BioRxiv. Aug. 27, 2018. doi.org/10.1101/401810.

Kuzyk et al., DNA-based self-assembly of chiral plasmonic nanostructures with tailored optical response. Nature. Mar. 14, 2012;483(7389):311-4. doi: 10.1038/nature10889.

Liedl et al., Controlled trapping and release of quantum dots in a DNA-switchable hydrogel. Small. Oct. 2007;3(10):1688-93. doi: 10.1002/smll.200700366.

Liu, Oligonucleotide-functionalized hydrogels as stimuli responsive materials and biosensors. Soft Matter. 2011. 7, 6757-6767. doi.org/10.1039/C1SM05284E.

Mitra et al., Fluorescent in situ sequencing on polymerase colonies. Anal Biochem. Sep. 1, 2003;320(1):55-65. doi: 10.1016/s0003-2697(03)00291-4.

Perrault et al., Virus-inspired membrane encapsulation of DNA nanostructures to achieve in vivo stability. ACS Nano. May 27, 2014;8(5):5132-40. doi: 10.1021/nn5011914. Epub Apr. 22, 2014.

Pinheiro et al., Challenges and opportunities for structural DNA nanotechnology. Nat Nanotechnol. Nov. 6, 2011; 6(12):763-72. doi: 10.1038/nnano.2011.187.

Rothemund, Folding DNA to create nanoscale shapes and patterns. Nature. Mar. 16, 2006;440(7082):297-302. doi: 10.1038/nature04586.

Zhang et al., Dynamic DNA nanotechnology using strand-displacement reactions. Nat Chem. Feb. 2011;3(2):103-13. doi: 10.1038/nchem.957.

Zhao et al., DNA origami delivery system for cancer therapy with tunable release properties. ACS Nano. Oct. 23, 2012;6(10):8684-91. doi: 10.1021/nn3022662. Epub Sep. 13, 2012.

* cited by examiner

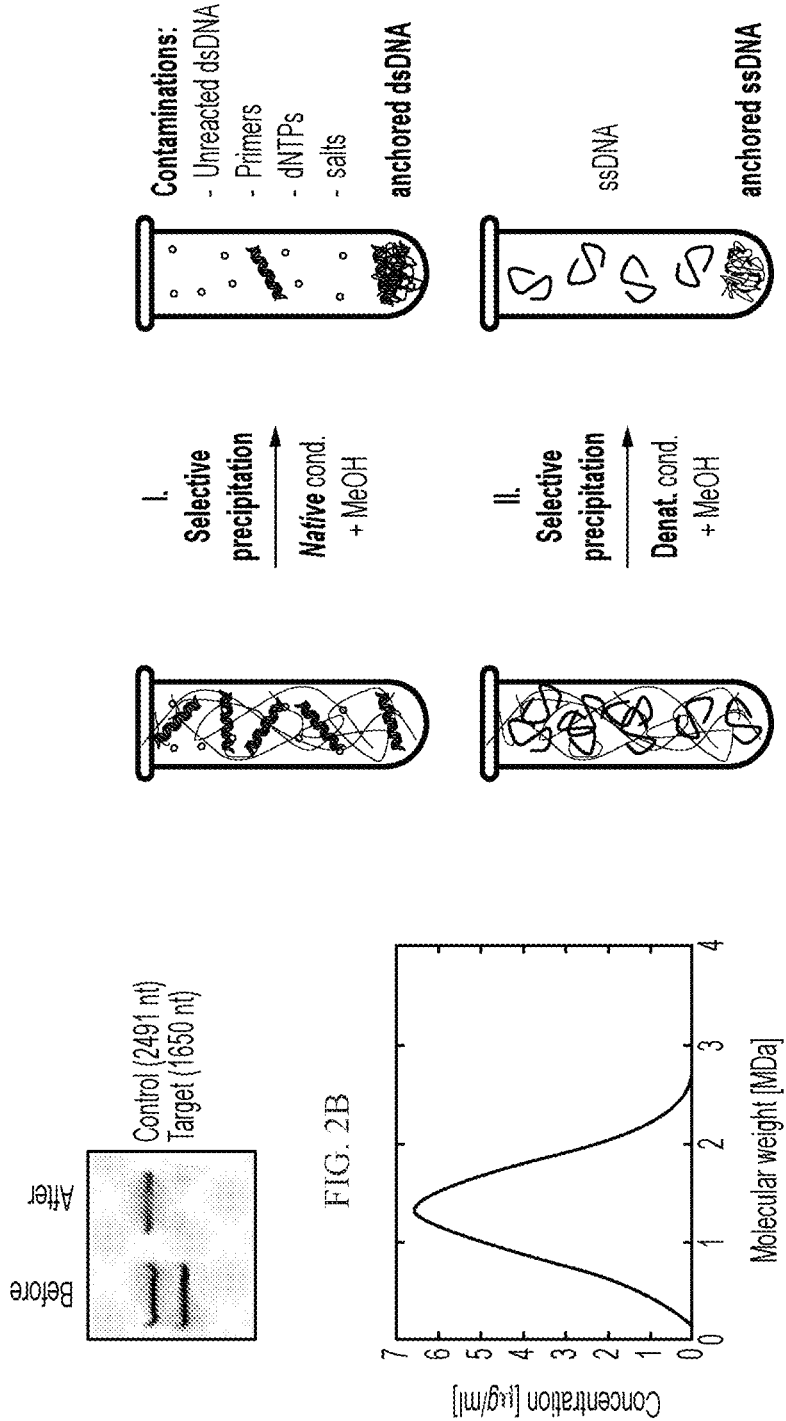

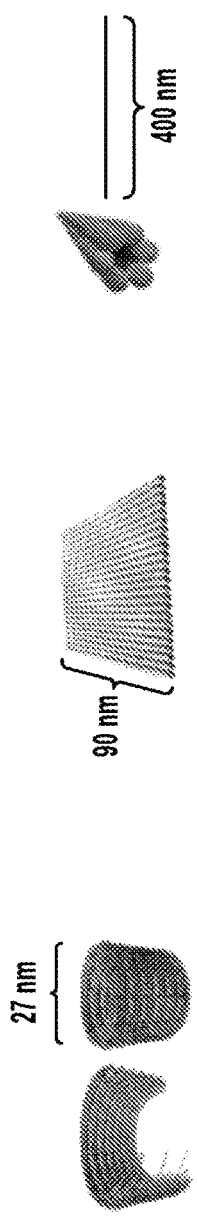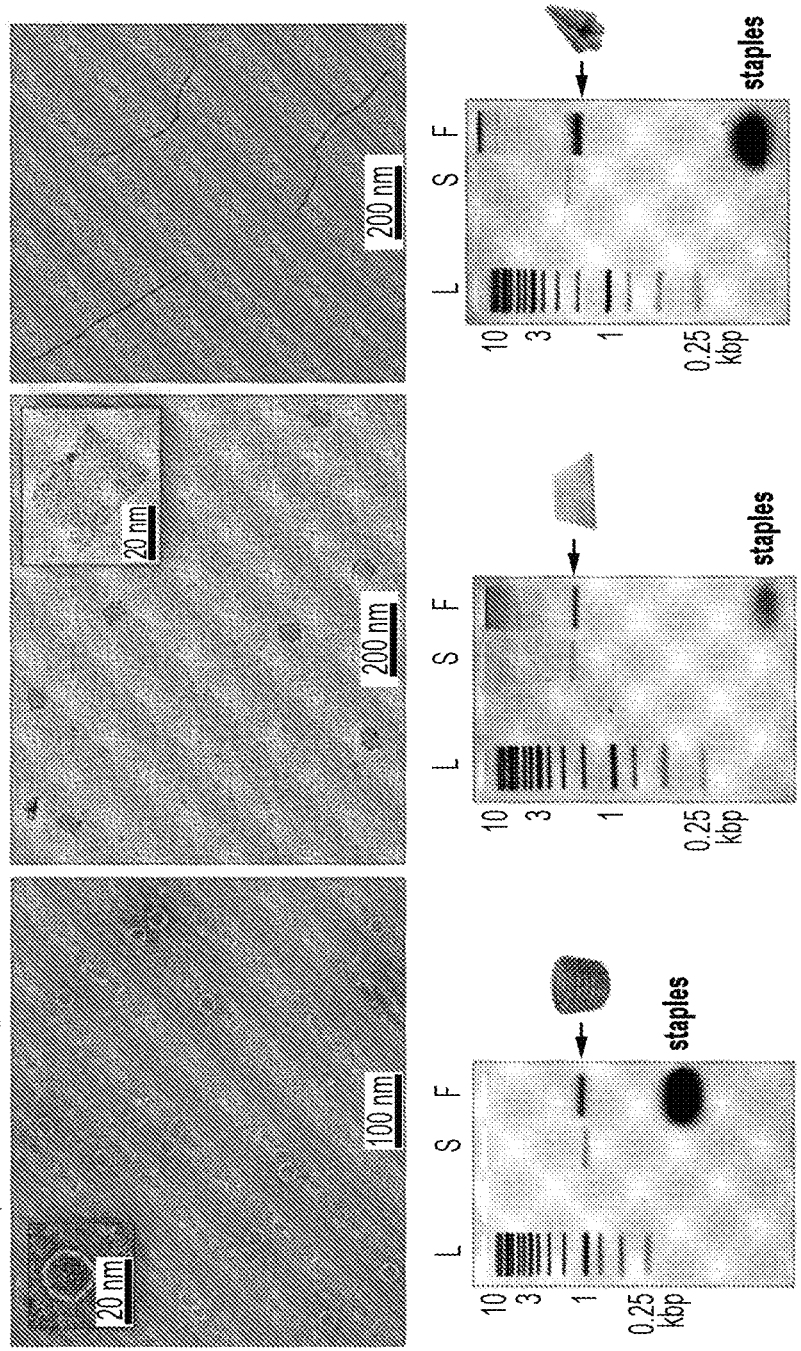
FIG. 3A  FIG. 3B  FIG. 3C

SEQUENCE LISTING

<160> NUMBER OF SEQ ID NOS: 3

<210> SEQ ID NO 1
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 1
cttacactgg tgtaagcgcg                                           20

<210> SEQ ID NO 2
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 2
tagccaacaa cgcgcttaca ccagtgtaag                                30

<210> SEQ ID NO 3
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 3
cttacactgg tgtaagcgcg ttgttggcta                                30
```

ACRYLAMIDE COPOLYMERIZATION FOR SEQUESTRATION AND PRODUCTION OF SINGLE-STRANDED NUCLEIC ACID

RELATED APPLICATION

This application is a national stage filing under 35 U.S.C. § 371 of international application number PCT/US2017/050929, filed Sep. 11, 2017, which was published under PCT Article 21(2) in English and claims the benefit under 35 U.S.C. § 119(e) of U.S. provisional application No. 62/393,600, filed Sep. 12, 2016, each of which is incorporated by reference herein in its entirety.

GOVERNMENT SUPPORT

This invention was made with government support under Grant No. 1435964 awarded by the National Science Foundation. The government has certain rights in the invention.

BACKGROUND

DNA plays a pivotal role in nature, as it encodes the genetic information in all living organisms. As such, methods to synthesize, amplify, selectively isolate and manipulate DNA strands are critical to biological and biomedical research, clinical diagnostics and therapeutics. Beyond its tremendous biological importance, DNA has intriguing properties for material applications because DNA is a stable polymer that can be programmed to assemble into well-defined nanostructures. The field of structural DNA nanotechnology has emerged over the last three decades, producing a large number of increasingly complex DNA-based nanosystems.[1] For example, the DNA-origami method uses multiple-kilobase-long single-stranded DNA "scaffolds" that fold into nearly arbitrary one-, two- or three-dimensional structures. DNA origami nanostructures have promising applications as drug delivery vehicles,[3-6] plasmonic systems,[7] devices for detection, computing,[8] and diagnostics.[9-11]

SUMMARY

The present disclosure provides methods, compositions and kits for scalable production of single-stranded (ssDNA) having sequence lengths of up to several thousand nucleotides (e.g., at least 7 kilobases). Experimental results disclosed herein show that (1) dsDNA may be sequestered in solution to form a copolymer containing the dsDNA, using a solution-phase polymerization process of the present disclosure, (2) ssDNA may be released by exposing the dsDNA copolymer to denaturation (dehybridization) conditions, and (3) methanol may then be used to selectively precipitate the copolymer in solution in the presence of the ssDNA, without precipitating the ssDNA. Thus, provided herein, in some embodiments, are efficient, cost-effective methods for producing in solution from dsDNA starting material long stretches of highly-pure ssDNA. FIGS. 4A-4B show a summary of an example of a solution-phase polymerization process double-stranded DNA (dsDNA) that includes dsDNA sequestration to form a copolymer, followed by ssDNA release from the copolymer—each step performed in solution.

Though structural DNA nanotechnology has the exciting potential to transform the field of material science, one key obstacle currently impeding the use of DNA-based nanomaterials for many real-life applications is the difficulty in producing ssDNA. While molecular biology offers powerful methods for the production of dsDNA,[12] the production of ssDNA—the building block of virtually all DNA-based materials—is expensive and difficult to perform on a large scale, especially when long (e.g., >90 nucleotide) strands with high purity are required. Provided herein, in some embodiments, are low cost methods, compositions and kits for the synthesis of large quantities of highly pure, long ssDNA.

Methods disclosed herein are useful, for example, for the production of long ssDNA for use as DNA origami templates as well as for the production of guide RNA (gRNA) templates. Methods for producing long, high-purity ssDNA strands can also be used as an upstream process to facilitate direct DNA sequencing having long read lengths. Moreover, methods, as provided herein, should enable screening of large libraries of ssDNA strands, for example, screening for deoxyribozyme activities or aptamer binding via systematic evolution of ligands by exponential enrichment (SELEX).[13] Large-scale ssDNA production should enable new DNA-based therapeutics (e.g., antisense) for treating cancer, HIV, diabetes, and other diseases as well as expand the scope of applications in DNA nanotechnology, CRISPR/Cas9-mediated genome editing, in vitro transcription, and ssDNA library construction.

Advantageously, small, nanometer-sized monomers such as acrylamide can rapidly access a reactive tag on the dsDNA target, without requiring conformational changes of the macromolecule; the polymer's capacity for DNA binding is very large, due to its massive molecular surface area per unit weight; and polyacrylamide (PAA) forms a homogeneous solution with low nonspecific binding affinity to DNA.

In addition to ssDNA production, the methods, compositions and kits of the present disclosure can be used for selective capture and release of a large variety of nucleic acid (e.g., DNA)-labeled targets (e.g., nucleic acids or proteins), which enables a wide range of biotechnological applications.

Thus, in some embodiments, provided herein are methods of producing single-stranded deoxyribonucleic acid (ssDNA), comprising: (a) combining in solution acrylamide-labeled double-stranded deoxyribonucleic acid (dsDNA) and acrylamide (AA) to form copolymer-linked dsDNA; (b) dehybridizing the copolymer-linked dsDNA to produce in solution free ssDNA and DNA-containing copolymer; and (c) separating the free ssDNA from the solution of (b).

Also provided herein, in some embodiments, are methods of target capture, comprising: combining, in solution comprising a target nucleic acid, acrylamide-labeled oligonucleotides having a nucleotide sequence complementary to a nucleotide sequence of the target nucleic acid, to form a captured target nucleic acid; and separating the captured target nucleic acid from the solution. In some embodiments, the methods of target capture comprise: combining, in solution comprising a target linked to a oligonucleotide label, and acrylamide-labeled oligonucleotides having a nucleotide sequence complementary to a nucleotide sequence of the oligonucleotide label, to form a captured target; and separating the captured target from the solution.

The present disclosure further provides kits comprising acrylamide monomers, ammonium persulfate (APS), tetramethylethylenediamine (TEMED), and methanol. In some embodiments, a kit further comprises acrylamide-labeled nucleic acid.

Compositions are also provided herein, including, for example, aqueous composition comprising a crosslinked copolymer having a molecular weight of at least 1000 kDa and linked to nucleic acids, and acrylamide (AA) and bisacrylamide (BAA), wherein the ratio of AA:BAA in the aqueous composition is less than 100:1. Other compositions may comprise a linear copolymer comprising acrylamide and acrylamide-labeled double-stranded deoxyribonucleic acid (dsDNA) having a length of at least 1000 nucleotide base pairs.

BRIEF DESCRIPTION OF THE DRAWINGS

FIGS. 2A-2E show schematics of Nascent Polyacrylamide Anchoring of dsDNA and isolation of ssDNA. FIG. 2A: Agarose gel electrophoresis of filtrates of an acrylamide-labeled 1650-nt target dsDNA in the presence of an unlabeled 2491-nt dsDNA control strand before and after sequestration via Route X. FIG. 2B: Molecular weight distribution of the linear copolymer (L) produced in sequestration via Route L. FIG. 2C: Schematic isolation of ssDNA by two-step precipitation in Route L: Selective precipitation of L under native conditions removes unreacted dsDNA and other contaminations (step I). A second precipitation of re-dispersed L under denaturing conditions isolates ssDNA from the copolymer (step II). FIG. 2D: Agarose gel analysis of supernatants obtained in steps I and II. Right side: photograph of the polymer pellet in a centrifuge tube. FIG. 2E: Agarose gel analyses of final ssDNA products in TE buffer.

FIGS. 3A-3C shows DNA origami folded from a NPA-produced scaffold. Origami design (top), TEM images (center), and corresponding agarose gels (bottom) of folded barrels (crude product mixture) (FIG. 3A), rectangles (excised from major product band) (FIG. 3B), and 6-helix bundles (excised from major product band) (FIG. 3C). L=dsDNA ladder, S=Scaffold, F=Folded structure.

FIG. 6A shows selective capture and release of target strands. FIG. 6B shows selective capture and removal of contaminants.

FIG. 15A shows ssCW0 obtained via a HMWCC route and subsequent ultracentrifugation with 70% yield. FIG. 15B shows ssCW1 obtained via a LC route and subsequent selective precipitation with 71% yield (FIG. 15B). L=1 kB DNA ladder (New England Biolabs).

DETAILED DESCRIPTION

Figure 4A:
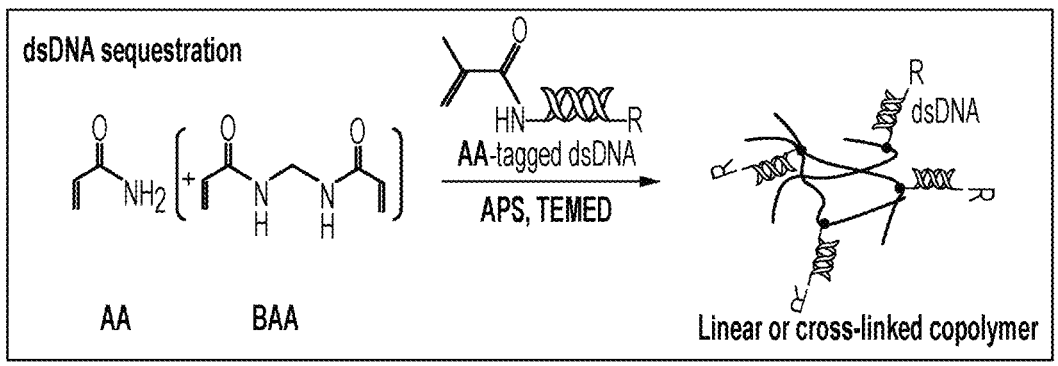
FIGS. 4A-4B show a schematic outlining the principle of dsDNA sequestration in solution-phase via acrylamide copolymerization (FIG. 4A) and subsequent ssDNA release (FIG. 4B). AA=Acrylamide; BAA=N,N'-Methylenebisacrylamide; APS=Ammonium persulfate; TEMED=Tetramethylethylenediamine.
Figure 4B:
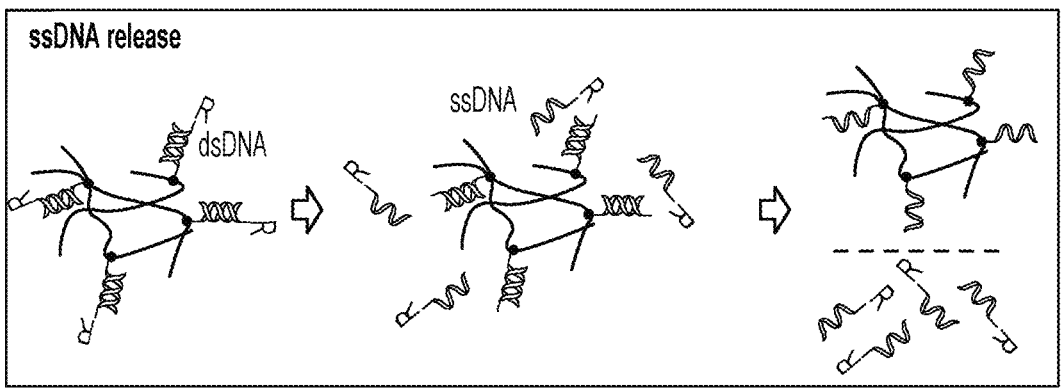

The methods, compositions and kits, as provided herein, enable production of preparative quantities of ssDNA with arbitrary sequences of up to several thousand nucleotides. An example of a method of the present disclosure includes dsDNA sequestration and ssDNA release in solution (FIGS. 4A-4B). Copolymerization of acrylamide-tagged dsDNA with acrylamide monomers forms a linear copolymer (LC) linked to dsDNA or a high molecular weight crosslinked copolymer (HMWCC) linked to dsDNA (FIG. 4A). Unreacted DNA, acrylamide monomers, and other reagents can be removed from the mixture by selective precipitation of the copolymer or by electroelution in an optional purification step. The dsDNA is denatured (dehybridized) (FIG. 4B, first step) to release ssDNA in solution. The copolymer is then removed from the solution containing free ssDNA (FIG. 4B, second step) by filtration, centrifugation, or selective precipitation. Finally, the free ssDNA is isolated.

Sequestration

An initial step of a method, as provide herein, includes sequestration in solution of acrylamide monomers and acrylamide-labeled double-stranded (dsDNA) to form copolymer-linked dsDNA. Acrylamide copolymerization, which produces polyacrylamide (PAA), is robust, has virtually unlimited loading capacity and does not require high purity of the precursor. Further, PAA is a biocompatible polymer with low nonspecific binding to DNA and other biomacromolecules. Thus, PAA is an ideal sequestration material, as it exhibits weak nonspecific binding, even for long DNA strands. When acrylamide monomers are combined with acrylamide-labeled dsDNA in solution, for example, in a solution comprising ammonium persulfate and tetramethylethylenediamine, a linear copolymer of polyacrylamide containing dsDNA is formed. With the addition of a crosslinking agent, such as bisacrylamide (BAA), a high molecular weight crosslinked copolymer is formed (the linear copolymer strands are crosslinked to each other in the presence of a crosslinking agent).

Acrylamide monomers (e.g., $C_3H_5NO$) are commercially available and are typically used to produce copolymers of polyacrylamide. The concentration of acrylamide monomers in a solution may be, for example, 5-500 mg/ml (0.5-50 wt %). In some embodiments, the concentration of acrylamide monomers in a solution is 10-500 mg/ml, 10-450 mg/ml, 10-400 mg/ml, 10-350 mg/ml, 10-300 mg/ml, 10-250 mg/ml, 10-200 mg/ml, 10-150 mg/ml, 10-100 mg/ml, 10-50 mg/ml, 10-25 mg/ml, 5-500 mg/ml, 5-450 mg/ml, 5-400 mg/ml, 5-350 mg/ml, 5-300 mg/ml, 5-250 mg/ml, 5-200 mg/ml, 5-150 mg/ml, 5-100 mg/ml, 5-50 mg/ml, 5-25 mg/ml or 5-10 mg/ml. For example, the concentration of acrylamide monomers in a solution may be 5, 10, 15, 20, 25, 30, 35, 40, 45, 50, 55, 60, 65, 70, 75, 80, 85, 90, 95, 100, 125, 150, 175, 200, 250, 300, 350, 400, 450 or 500 mg/ml of the solution.

In some embodiments, the concentration of acrylamide monomers in a solution is 1-50 wt %, 1-45 wt %, 1-40 wt %, 1-35 wt %, 1-30 wt %, 1-25 wt %, 1-20 wt %, 1-15 wt %, 1-10 wt %, 1-5 wt %, 1-2.5 wt %, 0.5-50 wt %, 0.5-45 wt %, 0.5-40 wt %, 0.5-35 wt %, 0.5-30 wt %, 0.5-25 wt %, 0.5-20 wt %, 0.5-15 wt %, 0.5-10 wt %, 0.5-5 wt %, 0.5-2.5 wt % or 0.5-1 wt %. For example, the concentration of acrylamide monomers in a solution may be 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 12.5, 15.0, 17.5, 20.0, 25.0, 30.0, 35.0, 40.0, 45.0 or 50.0 wt % of the solution.

In some embodiments, the concentration of acrylamide monomers in solution for the production of a linear copolymer (LC) is 40-60 mg/ml (e.g., 50 mg/ml) (or 4-6 wt %). In some embodiments, the concentration of acrylamide monomers in solution for the production of a high molecular weight crosslinked copolymer (HMWCC) is 10-15 mg/ml (e.g., 12.5 mg/ml) (or 1-1.5 wt %).

Acrylamide-labeled oligonucleotides are commercially available, chemically stable, and tolerate the thermal cycling conditions of polymerase chain reaction (PCR). Acrylamide-labeled dsDNA, like acrylamide-labeled oligonucleotides, may also be purchased from a commercial supplier or prepared using PCR, however, these sources can be expensive, especially when large quantities of acrylamide-labeled dsDNA are required. Thus, the present disclosure also provides an enzyme-free, and therefore inexpensive, method for preparing acrylamide-labeled dsDNA. The disclosed method can be used to readily produce preparative quantities of long (e.g., longer than 10 kb, 20 kb, 30 kb, 40 kb or 50 kb), acrylamide-labeled dsDNA. The disclosed methods may also be used to produce shorter acrylamide-labeled dsDNA (e.g., 0.1-10 kb, 0.2 kb, 0.5 kb, 1 kb, 2 kb or 5 kb).

Figure 5:
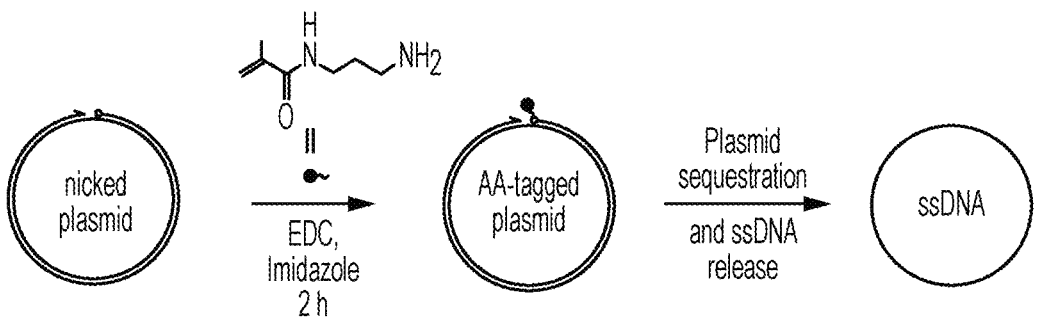
FIG. 5 shows a schematic of production of circular single-stranded DNA from a nicked plasmid precursor.

FIG. 5 provides a schematic outlining a method for preparing acrylamide-labeled dsDNA. A plasmid comprising a deoxyriboyzme domain catalyzes hydrolysis of its own phosphodiester backbone upon addition of zinc ions.[36,37] The resulting plasmid is nicked and, thus, contains a single 5' phosphate on one of its strands. This terminus can then be activated by N-ethyl-N'-(3-dimethylaminopropyl)carbodiimide (EDC) in the presence of imidazole,[38] and chemically functionalized with N-(3-aminopropyl)methacrylamide, thereby producing acrylamide-labeled dsDNA. The acrylamide-labeled dsDNA may then be sequestered in a copolymer, dehybridized, and circular ssDNA obtained following selective precipitation of the copolymer, as outlined below.

The concentration of acrylamide-labeled dsDNA (or other acrylamide-labeled nucleic acid, e.g., oligonucleotide) in a solution may be, for example, 0.01-10 mg/ml of the solution. In some embodiments, the acrylamide-labeled dsDNA concentration is 0.01-10 mg/ml, 0.01-9 mg/ml, 0.01-8 mg/ml, 0.01-7 mg/ml, 0.01-6 mg/ml, 0.01-5 mg/ml, 0.01-4 mg/ml, 0.01-3 mg/ml, 0.01-2 mg/ml, 0.01-1 mg/ml. In some embodiments, the acrylamide-labeled dsDNA concentration is 0.1-10 mg/ml, 0.1-9 mg/ml, 0.1-8 mg/ml, 0.1-7 mg/ml, 0.1-6 mg/ml, 0.1-5 mg/ml, 0.1-4 mg/ml, 0.1-3 mg/ml, 0.1-2 mg/ml, 0.1-1 mg/ml, 0.2-10 mg/ml, 0.2-9 mg/ml, 0.2-8 mg/ml, 0.2-7 mg/ml, 0.2-6 mg/ml, 0.2-5 mg/ml, 0.2-4 mg/ml, 0.2-3 mg/ml, 0.2-2 mg/ml, 0.2-1 mg/ml, 0.3-10 mg/ml, 0.3-9 mg/ml, 0.3-8 mg/ml, 0.3-7 mg/ml, 0.3-6 mg/ml, 0.3-5 mg/ml, 0.3-4 mg/ml, 0.3-3 mg/ml, 0.3-2 mg/ml, 0.3-1 mg/ml, 0.4-10 mg/ml, 0.4-9 mg/ml, 0.4-8 mg/ml, 0.4-7 mg/ml, 0.4-6 mg/ml, 0.4-5 mg/ml, 0.4-4 mg/ml, 0.4-3 mg/ml, 0.4-2 mg/ml, 0.4-1 mg/ml, 0.5-10 mg/ml, 0.5-9 mg/ml, 0.5-8 mg/ml, 0.5-7 mg/ml, 0.5-6 mg/ml, 0.5-5 mg/ml, 0.5-4 mg/ml, 0.5-3 mg/ml, 0.5-2 mg/ml, 0.5-1 mg/ml, 0.6-10 mg/ml, 0.6-9 mg/ml, 0.6-8 mg/ml, 0.6-7 mg/ml, 0.6-6 mg/ml, 0.6-5 mg/ml, 0.6-4 mg/ml, 0.6-3 mg/ml, 0.6-2 mg/ml, 0.6-1 mg/ml, 0.7-10 mg/ml, 0.7-9 mg/ml, 0.7-8 mg/ml, 0.7-7 mg/ml, 0.7-6 mg/ml, 0.7-5 mg/ml, 0.7-4 mg/ml, 0.7-3 mg/ml, 0.7-2 mg/ml, 0.7-1 mg/ml, 0.8-10 mg/ml, 0.8-9 mg/ml, 0.8-8 mg/ml, 0.8-7 mg/ml, 0.8-6 mg/ml, 0.8-5 mg/ml, 0.8-4 mg/ml, 0.8-3 mg/ml, 0.8-2 mg/ml, or 0.8-1 mg/ml, of the solution. In some embodiments, the concentration of acrylamide-labeled dsDNA is 1-5 mg/ml, 1-4 mg/ml, 1-3 mg/ml, or 1-2 mg/ml of the solution. In some embodiments, the acrylamide-labeled dsDNA concentration is 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml or 10 mg/ml of the solution.

The methods and compositions of the present disclosure are particularly useful for the production of long ssDNA (although the methods and compositions may also be used for producing shorter ssDNA, e.g., less than 100 nucleotide base pairs), which is produced from a long acrylamide-labeled dsDNA template. Thus, the length of acrylamide-labeled double-stranded (dsDNA) in a solution, in some embodiments, is at least 100 nucleotide base pairs (bp). For example, the length of an acrylamide-labeled dsDNA may be 100-1000 bp, 100-5000 bp, 100-10000 bp, 100-25000 bp, or 100-50000 bp. In some embodiments, the length of an acrylamide-labeled dsDNA is 1000-50000 bp, 1000-25000 bp, 1000-10000 bp, 1000-5000 bp, or 1000-2000 bp. In some embodiments, the length of an acrylamide-labeled dsDNA is 100, 200, 300, 400, 500, 600, 700, 800, 900, 1000, 1500, 2000, 2500, 3000, 3500, 4500, 5000, 5500, 6000, 6500, 7000, 7500, 8000, 8500, 9000, 9500 or 10000 bp. In some embodiments, the length of an acrylamide-labeled dsDNA is greater than 50000 bp, or shorter than 100 bp. In some embodiments, the length of an acrylamide-labeled dsDNA is 10-100 bp.

A solution (e.g., a sequestration solution) that comprises acrylamide polymers and acrylamide-labeled dsDNA must also comprise a reagent that initiates copolymer formation. For example, a sequestration solution may comprise ammonium persulfate (APS), tetramethylethylenediamine (TEMED), or a combination of APS and TEMED to catalyze the polymerization of acrylamide to form a polyacrylamide copolymer. Other similar reagents are encompassed by the present disclosure, including, but not limited to: riboflavin and TEMED; riboflavin, APS and TEMED; APS and metabisulfite; APS, nitrotris(propionamide), and sodium sulfate; or APS and ammonium ferrous sulfate.

The concentration of APS and TEMED in a sequestration solution may vary between 0.0005 wt % and 0.2 wt %, for example, depending in part on the intended copolymer and on the presence (or absence) or oxygen. For sequestration of acrylamide-labeled dsDNA to form a linear copolymer (LC) protected from oxygen, the APS concentration may be 0.01 wt %-0.1 wt %. In some embodiments, the APS concentration is 0.01 wt %, 0.02 wt %, 0.03 wt %, 0.04 wt %, 0.05 wt %, 0.06 wt %, 0.07 wt %, 0.08 wt %, 0.09 wt %, or 0.10 wt %. In some embodiments, the APS concentration is 0.05 wt %. Likewise, for sequestration of acrylamide-labeled dsDNA to form a LC protected from oxygen, the TEMED concentration may be 0.01 wt %-0.1 wt %. In some embodiments, the TEMED concentration is 0.01 wt %, 0.02 wt %, 0.03 wt %, 0.04 wt %, 0.05 wt %, 0.06 wt %, 0.07 wt %, 0.08 wt %, 0.09 wt %, or 0.10 wt %. In some embodiments, the TEMED concentration is 0.05 wt %.

For sequestration of acrylamide-labeled dsDNA to form a high molecular weight crosslinked copolymer (HMWCC) protected from oxygen, the APS concentration may be 0.01 wt %-0.1 wt %. In some embodiments, the APS concentration is 0.01 wt %, 0.02 wt %, 0.03 wt %, 0.04 wt %, 0.05 wt %, 0.06 wt %, 0.07 wt %, 0.08 wt %, 0.09 wt %, or 0.10 wt %. In some embodiments, the APS concentration is 0.05 wt % Likewise, for sequestration of acrylamide-labeled dsDNA to form a HMWCC protected from oxygen, the TEMED concentration may be 0.01 wt %-0.1 wt %. In some embodiments, the TEMED concentration is 0.01 wt %, 0.02 wt %, 0.03 wt %, 0.04 wt %, 0.05 wt %, 0.06 wt %, 0.07 wt %, 0.08 wt %, 0.09 wt %, or 0.10 wt %. In some embodiments, the TEMED concentration is 0.05 wt %.

In the presence of oxygen concentrations of APS and TEMED may be 0.05 wt %-0.2% wt %. For example, the APS and/or the TEMED concentration in the presence of oxygen may be 0.05 wt %, 0.06 wt %, 0.07 wt %, 0.08 wt %, 0.09 wt %, 0.10 wt %, 0.11 wt %, 0.12 wt %, 0.13 wt %, 0.14 wt %, 0.15 wt %, 0.16 wt %, 0.17 wt %, 0.18 wt %, 0.19 wt % or 0.20 wt %.

Various crosslinking agents may be added to a sequestration solution to produce crosslinked copolymer. In some embodiments, the crosslinking reagent comprises bisacrylamide (BAA). In some embodiments, the crosslinking reagent comprises N,N'-methylenebisacrylamide (or $C_7H_{10}N_2O_2$). In some embodiments, the crosslinking reagent comprises piperazine diacrylamide, N,N'(hexamethylenebis(methacrylamide), N,N'-ethylenebis(acrylamide) or combinations thereof.

A sequestration solution may comprises a AA:BAA ratio of greater than 1:1. In some embodiments, a AA:BAA ratio is 1:1 to 200:1. For example, a AA:BAA ratio may be 200:1, 190:1, 180:1, 170:1, 160:1, 150:1, 140:1, 130:1, 120:1, 120:1, 100:1, 90:1, 80:1, 70:1, 60:1, 50:1, 40:1, 30:1, 20:1, 10:1, 9:1, 8:1, 7:1, 6:1, 5:1, 4:1, 3:1, 2:1 or 1:1. In some embodiments, a ratio of AA:BAA is greater than 200:1.

Copolymer-linked dsDNA, as described above, may be produced by combining acrylamide monomers and acrylamide-labeled dsDNA in a sequestration solution. One of two different copolymers may be produced depending on the presence or absence of a crosslinking agent. In general, a "copolymer-linked dsDNA" refers to a composition comprising acrylamide linked to (attached to) acrylamide-labeled dsDNA. In the absence of a crosslinking agent, and, in some embodiments, in the presence of acrylate, a linear polymer containing acrylamide-acrylamide bonds as well as sequestered dsDNA is formed, which is referred to as a "linear copolymer (LC)." In the presence of a crosslinking agent (and by varying the concentration of reagents that initiate copolymer formation), the linear copolymers are crosslinked to each other and a "high molecular weight crosslinked copolymer (HMWCC)" is formed. A HMWCC may have a molecular weight of, for example, at least 1 kDa (kilodaltons), at least 10 kDa, at least 100 kDa or at least 1000 kDa.

A copolymer may comprise, for example, acrylamide, bisacrylamide, acrylate, sodium acrylate, or other acrylic monomers. In some embodiments, a copolymer comprises acrylamide and acrylate. In other embodiments, a copolymer comprises acrylamide and bisacrylamide.

A linear copolymer, in some embodiments, is produced using a solution of acrylamide and acrylate. The ratio of acrylamide to acrylate may be 50:1 to 200:1. For example, the ratio of acrylamide to acrylate in solution may be 50:1, 60:1, 70:1, 80:1, 90:1, 100:1, 110:1, 120:1, 130:1, 140:1, 150:1, 160:1, 170:1, 180:1, 190:1 or 200:1. In some embodiments, the ratio of acrylamide to acrylate is 91:1, 92:1, 93:1, 94:1, 95:1, 96:1, 97:1, 98:1, 99:1, 100:1, 101:1, 102:1, 103:1, 104:1 or 105:1. In some embodiments, the ratio of acrylamide to acrylate is at least 99:1. In some embodiments, the ratio of acrylamide to acrylate is 99:1.

Advantageously, the methods provided herein produce copolymers that comprise a high percentage of the dsDNA starting material. In some embodiments, a copolymer-linked dsDNA may comprise at least 80% of the acrylamide-labeled dsDNA from a sequestration solution (at least 80% of the acrylamide-labeled dsDNA starting material). For example, a copolymer-linked dsDNA may comprise at least 85%, at least 90%, or at least 95% of the acrylamide-labeled dsDNA from a sequestration solution. In some embodiments, a copolymer-linked dsDNA may comprises 50-90%, 55-90%, 60-90%, 65-90%, 70-90%, 75-90%, 80-90%, 85-90%, 50-95%, 55-95%, 60-95%, 65-95%, 70-95%, 75-95%, 80-95%, 85-95%, 50-100%, 55-100%, 60-100%, 65-100%, 70-100%, 75-100%, 80-100%, 85-100%, 90-100%, or 95-100% of the acrylamide-labeled dsDNA from a sequestration solution.

A sequestration reaction may be performed "under conditions that result in formation of a copolymer containing dsDNA." It should be understood that such conditions are described throughout the present disclosure and take into account the type and concentration of the disclosed reagents as well as incubation times and temperatures.

Thus, a sequestration solution (e.g., comprising acrylamide monomers, acrylamide-labeled dsDNA, APS, TEMED and optionally BAA) may be incubated at room temperature, for example, for 1-48 hours. In some embodiments, a sequestration solution is incubated for 1-6 hours, 1-8 hours, 1-12 hours, 1-24 hours, 1-36 hours, or 1-48 hours. Incubation time may depend on the type of intended copolymer.

For example, production of a linear copolymer may only require an incubation time of 2 hours or less. Thus, in some embodiments, a sequestration solution (e.g., without crosslinking agent) is incubated for 30 min, 1 hour, 1.5 hours, 2 hours or 2.5 hours. In some embodiments, a sequestration solution without crosslinking agent is incubated for 30 min-2.5 hours. In some embodiments, a sequestration solution without crosslinking agent is incubated for about 2 hours. For production of a crosslinked copolymer, the incubation time may be longer than 2 hours, for example, as long as 8 hours, or longer. Thus, in some embodiments, a sequestration solution (e.g., with crosslinking agent) is incubated for (or for at least) 6, 7, 8, 9, 10, 11, or 12 hours. In some embodiments, a sequestration solution with crosslinking agent is incubated for 6-12 hours. In some embodiments, a sequestration solution with crosslinking agent is incubated for about 8 hours.

Purification

In some instances, it may be advantageous to purify a copolymer (separate a copolymer from contaminants, such as unreacted acrylamide monomers or unreacted acrylamide-labeled DNA) following sequestration of acrylamide-linked dsDNA. Thus, in some embodiments a copolymer-linked dsDNA is purified following sequestration and prior to dehybridization. Surprisingly, the present disclosure shows that methanol may be used to selectively precipitate copolymer-linked dsDNA. For example, the addition of methanol having of volume of at least 2× (e.g., 2×, 2.5×, 3×, 3.5×, 4×, 4.5×, 5×) relative to the total volume of the sequestration solution results in selective precipitation of the copolymer-linked dsDNA species. Thus, in some embodiments, methods of the present disclosure comprise adding to a sequestration solution at least 2 volumes of methanol. In some embodiments, methods of the present disclosure comprise adding to a sequestration solution at least 3 volumes of methanol. The precipitate is then collected from solution and reconstituted in an aqueous buffer, for example. This solution of buffer and purified copolymer may then be subjected to denaturation/dehybridization, as described below.

Alternatively, a copolymer-linked dsDNA may be purified by conventional electroelution methods, whereby the sequestration solution is loaded a substrate, such as into the well of a gel (e.g., agarose gel), into electrolyte solution, onto a membrane, or into an electroelution chamber, and an electric current is applied to the substrate to elute contaminants into the substrate, for example.

As indicated above, this purification process (between sequestration and dehybridization) is optional. A method of producing ssDNA, for example, may proceed from a sequestration step(s) directly to the dehybridization step(s), discussed below.

Dehybridization

Following sequestration of dsDNA, the resulting copolymer-linked dsDNA (purified or unpurified) may be denatured to separate ssDNA from the copolymer-linked dsDNA. This denaturation process is referred to herein as "dehybridization." A copolymer-linked dsDNA may be dehybridized using any one of the following denaturation buffers: sodium hydroxide, formamide, dimethyl sulfoxide (DMSO) and/or urea. In some embodiments, a dehybridization buffer comprises: sodium hydroxide and ethylenediaminetetraacetic acid (EDTA); formamide and EDTA; or Tris-EDTA (in the presence of heat, e.g., 80-95° C.). Other denaturation buffers are encompassed by the present disclosure.

In some embodiments, a dehybridization solution comprises an alkaline solution, for example a basic dehybridization solution (e.g., BDS, 100 mM NaOH, 1 mM EDTA). In some embodiments, a dehybridization solution comprises a formamide solution, for example, a formamide dehybridization buffer (e.g., FDB, 95% (v/v) formamide, 5 mM EDTA, pH 8.1). In some embodiments, a dehybridization solution comprises dimethyl sulfoxide (DMSO). In some embodiments, a dehybridization solution comprises an aqueous buffer (e.g., Tris-EDTA, TE).

Dehybridization in solution may also include a heating step, for example, heating a dehybridization solution to 80-95° C. (e.g., 95° C.) for 2-5 minutes.

In some embodiments, a copolymer-linked dsDNA may be dehybridized using physical methods, such as sonication or agitation in the presence of glass beads.

Separation and ssDNA Retrieval

Following dehybridization of the copolymer-linked dsDNA to produce ssDNA, any remaining copolymer should be removed from the ssDNA-containing solution. This may be achieved using the selective precipitation method described above (e.g., for LC or HMWCC), or by centrifugation or microfiltration (e.g., for HMWCC). Removal of the copolymer from ssDNA-containing solution is referred to herein as "separation."

Thus, in some embodiments, methods of the present disclosure comprise adding methanol to a solution comprising, for example, dehybridization buffer, copolymer and ssDNA, to selectively precipitate the copolymer. For example, the addition of methanol having of volume of at least 2× (e.g., at least 2×, 2.5×, 3×, 3.5×, 4×, 4.5× or 5×) relative to the total volume of the solution results in selective precipitation of the copolymer species. Thus, in some embodiments, method of the present disclosure comprising adding to a solution comprising copolymer and ssDNA at least 2 volumes of methanol. In some embodiments, method of the present disclosure comprising adding to a solution comprising copolymer and ssDNA at least 3 volumes of methanol. The precipitate is then collected from solution, leaving a solution of ssDNA, referred to as herein as a "retrieval solution."

Alternatively, copolymer can be separated from ssDNA using microfiltration or centrifugation. In some embodiments, a solution comprising copolymer and ssDNA is passed over a microfiltration membrane to remove the copolymer. The microfiltration membrane may be, for example, a cellulosed acetate membrane or a polyethersulfone membrane. In some embodiments, a solution is subjected to centrifugation to remove the copolymer. A solution may be subjected to centrifugation speeds such as ultracentrifugation speeds of, for example, 100000-200000 g for 15-60 minutes.

This retrieval solution comprises ssDNA, which may be purified from the solution using standard ethanol or isopropanol precipitation protocols. For example, ssDNA can be purified by precipitation in an alcohol/retrieval solution mixture in the presence of a high concentration (e.g., 0.5-1M LiCl, 0.3-0.5M NaCl, NaOAc, or 2-3 M $NH_4Ac$) of inorganic salt and ethanol or isopropanol (e.g., 30%-50% final percentage isopropanol; 60%-80% final percentage ethanol), storage for a brief period of time at −20° C. or −70° C., followed by centrifugation. Subsequent desalting of the ssDNA pellet may comprise rinsing the pellet in 70% alcohol, recentrifugation and re-suspension in buffer or water.

Target System Capture

In addition to being able to produce long stretches of ssDNA, the methods of the present disclosure may be used in the context of target (e.g., nucleic acid or protein) capture.

Figure 6A:
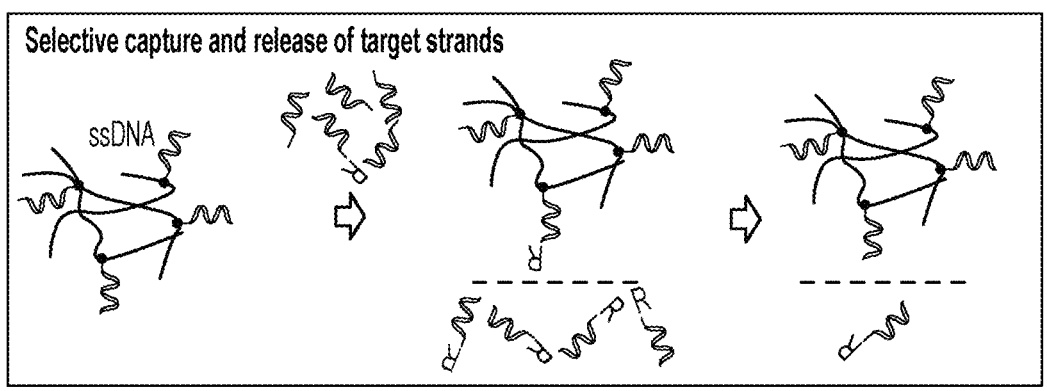
FIGS. 6A-6B show two related applications of acrylamide-DNA copolymers.
Figure 6B:
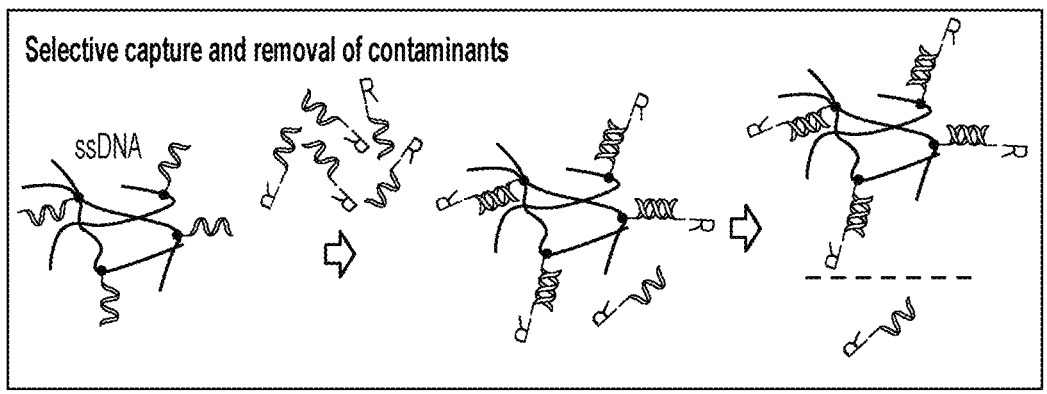

For example, when copolymerizing acrylamide-labeled oligonucleotides (e.g., single-stranded nucleic acids having a length of less the 200 nucleotides or less than 100 nucleotides) with acrylamide monomers, the resulting LC and HMWCC can be used to selectively scavenge specific target systems from the solution. An example of this method is depicted in FIG. 6A. The scavenged target can be released by thermal denaturation or chemical denaturation, or via a toehold-mediated strand displacement mechanism (Zhang D, et al., 2011 Nature Chemistry. 3 (2): 103-113, incorporated herein by reference). Similarly, as depicted in FIG. 6B, copolymerized oligonucleotide can be hybridized with a set of different adapter strands. Each adapter may provide a binding site that scavenges a specific library of complementary sequences. The possible number of strands in such a library is virtually unlimited.

Both methods are suitable for large-scale purifications of RNA, DNA, or DNA-labeled target systems. Such target systems could be, for example, DNA origami, covalently functionalized proteins or peptides. Moreover, the copolymerized oligonucleotide can be an aptamer that specifically scavenges unlabeled proteins from solution. Other target systems are encompassed herein.

Thus, the present disclosure provides methods of target capture, comprising combining, in solution comprising a target nucleic acid, acrylamide-labeled oligonucleotides having a nucleotide sequence complementary to a nucleotide sequence of the target nucleic acid, to form a captured target nucleic acid, and separating the captured target nucleic acid from the solution. The present disclosure also provides methods of target capture, comprising combining, in solution comprising a target linked to a oligonucleotide label, acrylamide-labeled oligonucleotides having a nucleotide sequence complementary to a nucleotide sequence of the oligonucleotide label, to form a captured target, and separating the captured target from the solution.

A sequence is "complementary to" another sequence if one sequence contains nucleotides that base pair (hybridize/bind through Watson-Crick nucleotide base pairing) with nucleotides of the other sequence such that the two sequences form a paired (double-stranded) or partially-paired molecular species/structure. In some embodiments, a sequence in an acrylamide-labeled oligonucleotide is described as "complementary to" a sequence in a target nucleic acid such that, by pairing up complementary regions, the nucleic acid becomes double-stranded, thereby capturing the target sequence. Complementary sequences need not be perfectly (100%) complementary to form a captured target, although perfect complementarity is provided in some embodiments.

In some embodiments, the acrylamide-labeled oligonucleotide may be at least two acrylamide-labeled oligonucleotides having distinct sequences that can be used to selectively scavenge distinct target nucleic acids, for example contaminants, from a solution (FIG. 6B). In some embodiments, the acrylamide-labeled oligonucleotides having distinct sequences may be at least 2, at least 3, at least 4, at least 5, at least 10, at least 25, or at least 50. In some embodiments, the oligonucleotide strands having distinct sequences may be at least 100, at least 250, at least 500, at least 1000, at least 2500, or at least 5000.

In some embodiments, a target nucleic acid may be RNA or DNA. In some embodiments, a target linked to an oligonucleotide label may be a target protein linked to an oligonucleotide. In some embodiments, a target nucleic acid may be a protein. For example, the acrylamide-labeled oligonucleotide can be an aptamer that specifically scavenges unlabeled protein targets from solution.

An acrylamide-labeled oligonucleotide may be single-stranded (ss) or double-stranded (ds). The acrylamide-labeled oligonucleotide may comprise DNA, RNA or a hybrid molecule, for example, where the oligonucleotide contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine. In some embodiments, the acrylamide-labeled oligonucleotide is DNA.

An acrylamide-labeled oligonucleotide of the present disclosure may include backbone modifications, base modifications, and/or sugar modifications. Examples of these modifications are known. In some embodiments, an acrylamide-labeled oligonucleotides comprise a backbone other than a phosphodiester backbone. For example, an acrylamide-labeled oligonucleotide, in some embodiments, may comprise phosphoramide, phosphorothioate, phosphorodithioate, O-methylphophoroamidite linkages, peptide nucleic acids or a combination of any two or more of the foregoing linkages.

Preparative Matrix-Assisted Asymmetric Polymerase Chain Reaction (PMA-PCR).

Figure 7:
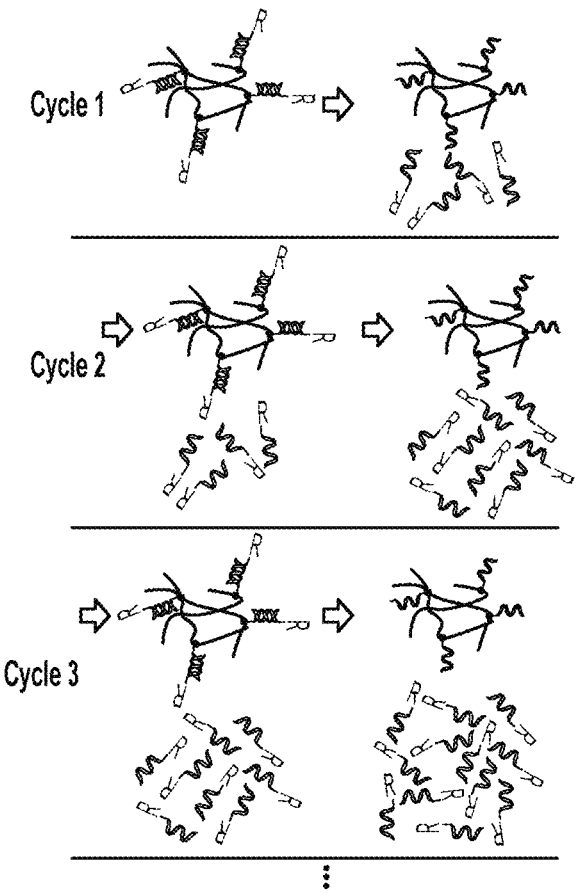
FIG. 7 shows a schematic of preparative matrix-assisted asymmetric polymerase chain reaction (PMA-PCR) that generates preparative amounts of single-stranded DNA over few PCR cycles using linear amplification of DNA at high concentrations, followed by separation of single-stranded product from the template copolymer.

Also provided herein is a preparative gel-phase asymmetric polymerase chain reaction (PMA-PCR) for the production of ssDNA. In PMA-PCR, the copolymer stays homogeneously dispersed in solution during the PCR reaction and the copolymer can easily be separated from the reaction product, thereby producing a ssDNA product that is separated from its complementary strand (FIG. 7). PMA-PCR may be performed using very high template concentrations, thus generating preparative amounts of ssDNA in a few PCR cycles. Fewer PCR cycles minimizes exposure of ssDNA to thermal damage that occurs during PCR.

Preparation of Guide RNA Template

While the present disclosure primarily describes the production of long stretches of ssDNA (e.g., for use in DNA origami methods), shorter stretches may also be produced. Such shorter stretches, for example, less than 100 nucleotides, may be useful for producing ssDNA that is used as template for the production of guide RNAs, which function to target Cas9 endonucleases (and similar endonucleases) to target nucleic acids (e.g., genomic/chromosomal nucleic acids). Thus, in some embodiments, provided herein are methods of producing guide RNA template, the methods comprising (a) combining in solution acrylamide-labeled double-stranded deoxyribonucleic acid (dsDNA) and acrylamide (AA) to form copolymer-linked dsDNA, (b) dehybridizing the copolymer-linked dsDNA to produce in solution free ssDNA and DNA-containing copolymer, and (c) separating the free ssDNA from the solution of (b), thereby producing ssDNA for use as a template for producing guide RNAs.

Kits

The present disclosure also provides kits for producing ssDNA, via dsDNA sequestration and ssDNA release, as well as kits for target capture. The kits comprising, in some embodiments, acrylamide monomers, APS, TEMED and methanol. In some embodiments, the kits further comprise acrylamide-labeled nucleic acid, such as acrylamide-labeled oligonucleotides (ssDNA having a length of less than 200 or less than 100 nucleotides) or acrylamide-labeled dsDNA (e.g., having a length of 10-100,000 nucleotides), The acrylamide-labeled dsDNA, in some embodiments, may be linear, while in other embodiments, the acrylamide-labeled dsDNA is circular.

In some embodiments, a kit further comprises a cross-linking agent, such as bisacrylamide (BAA). Kits may also comprise an aqueous buffer, such as comprises (i) sodium hydroxide and EDTA, (ii) formamide and EDTA, or (iii) Tris-EDTA. Other solutions, such as the dehybridization solutions described above, may be included in a kit.

In some embodiments, the kit further comprises ethanol or isopropanol.

In some embodiments, the kit further comprises a microfiltration membrane, such as a cellulosed acetate membrane or a polyethersulfone membrane. In some embodiments, the kit further comprises centrifuge tubes and/or a syringe needle.

In some embodiments, a kit component comprises instructions for producing ssDNA as described herein.

The components of the kit may be provided in any useful form. In some embodiments, components are provided as liquid solutions or as dried powders. In some embodiments, components provided as a dry powder may be reconstituted by the addition of an aqueous buffer, which may also be provided. In some embodiments, components provided as liquid solutions may be concentrated or ready to use.

EXAMPLES

Method for sequestration of ssDNA, as provided herein, include (e.g., FIGS. 1 and 4) include sequestration, purification, dehybridization and separation and retrieval of ssDNA. Sequestration involves copolymerization of acrylamide-labeled dsDNA with acrylamide monomers to form linear copolymers or crosslinked copolymers having a high molecular weight. Unreacted acrylamide-labeled dsDNA, acrylamide monomers, and other reagents can be optionally removed from the mixture by selective precipitation or by electroelution of the copolymer. The dsDNA is dehybridized under denaturing conditions and the copolymer is removed from the released ssDNA by filtration, centrifugation, or selective precipitation. Examples of the disclosed methods and compositions are described below.

Example 1: Nascent Polyacrylamide Anchoring (NPA)

Figure 1:
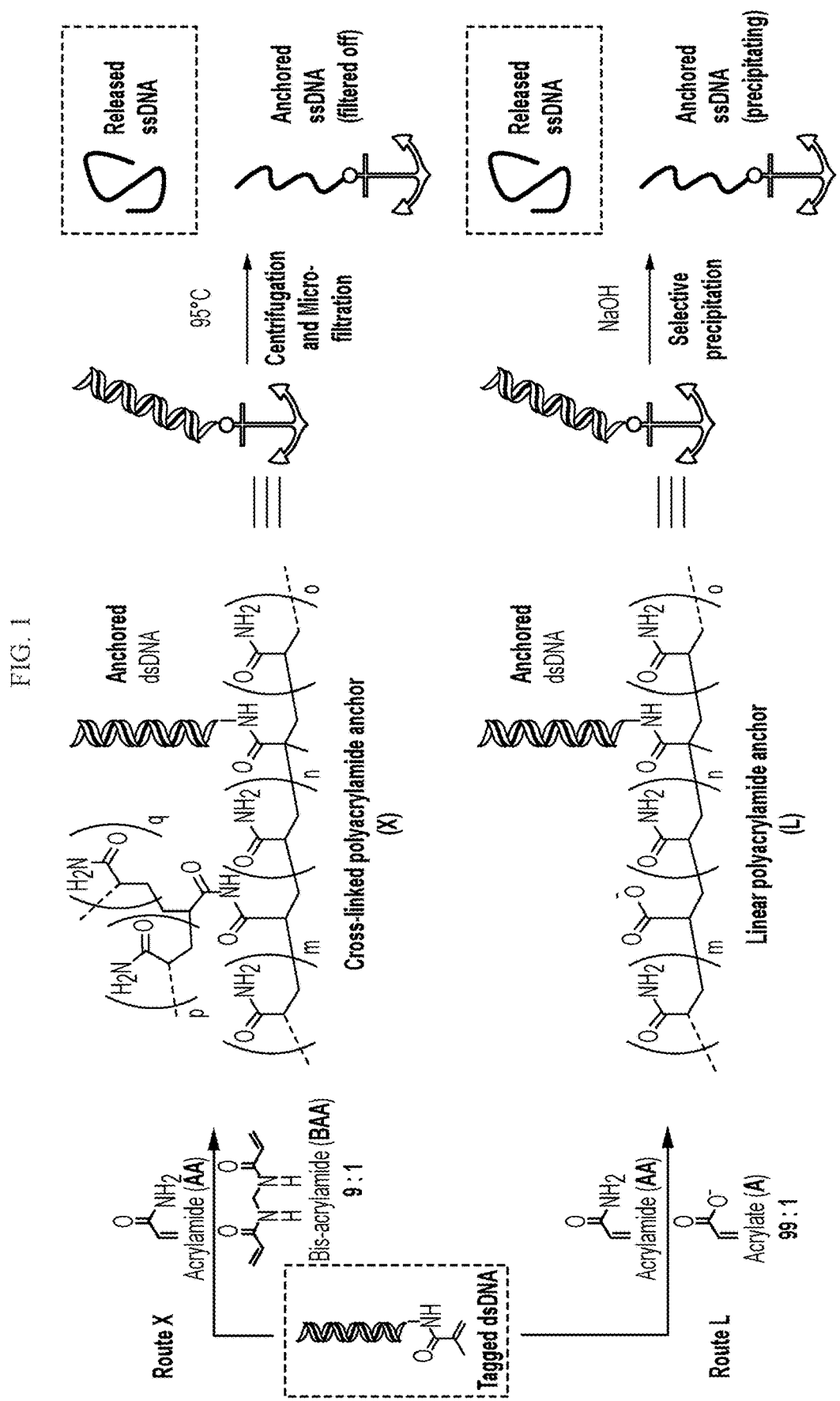
FIG. 1 shows a schematic of ssDNA production via Nascent Polyacrylamide Anchoring (NPA). Route X: Copolymerization of target DNA in presence of 9:1 (wt/wt) acrylamide/bis-acrylamide. Released ssDNA can be separated from its anchored complement by centrifugation and subsequent microfiltration. Route L: Copolymerization of target DNA in presence of 99:1 (wt/wt) acrylamide/acrylate. Released ssDNA is obtained by selective precipitation of its anchored complement.

The method provided herein, referred to as Nascent Polyacrylamide Anchoring (NPA), enables inexpensive and scalable production of ssDNA with strand lengths of up to several thousand nucleotides. The method relies on anchoring of acrylamide (AA)-labeled dsDNA by copolymerization with AA and acrylate (A) or bis-acrylamide (BAA) monomers, followed by dehybridization of the polymer-linked dsDNA, and subsequent separation of the released ssDNA from the high-molecular-weight copolymer by filtration, centrifugation, or selective precipitation of the latter (FIG. 1).

AA-DNA copolymers can be used for isolation of untagged ssDNA strands under alkaline denaturing conditions, due to efficient and selective precipitation by addition of methanol. AA-tagged dsDNA in the kilobase length range was generated by PCR on scales between 5 μg (in single PCR tubes) to 1.5 mg (in 96-well PCR plates). Strands shorter than 5 kbp were amplified by using regular forward primers, commercially available AA-labeled reverse primers, and inexpensive Taq polymerase. Longer dsDNA was produced via the use of high-fidelity, long-range polymerases.

NPA can be performed directly on the crude PCR product, except when organic solvent additives, detergents or thiols are present in the PCR reaction; in this case, these reagents can be removed beforehand by spin column treatment or ethanol precipitation. We developed two different NPA routes, Route X and Route L (FIG. 1). In both routes, the copolymerization step is (1) highly efficient and (2) selective for AA-labeled target strands: (1) we observe 90-97% incorporation of short oligonucleotides into the copolymer. Equally high efficiencies (~90-95%) were achieved for kilobase-long PCR amplicons. The copolymerization yield remained >90% even for DNA concentrations of 1000 ng/μL, demonstrating that this approach indeed provides extraordinarily high binding capacity. (2) AA-labeled oligonucleotides were selectively sequestered from solution in presence of unlabeled oligonucleotide truncation products, which are a common contamination in oligonucleotide synthesis. Similarly, long AA-labeled dsDNA (1.7 kbp) was selectively sequestered in presence of an unmodified dsDNA control, as revealed by agarose gel electrophoresis (AGE) of the solution before and after sequestration (FIG. 2A). Despite its large size, the control strand (2.5 kbp) was neither adsorbed nor entrapped within the inert PAA matrix.

Route X.

A cross-linked copolymer (X) is formed when the reaction mixture contains AA and BAA monomers. The radical polymerization is initiated by ammonium persulfate (APS) and catalyzed by tetramethylethylenediamine (TEMED). It was thought that X could be removed size-selectively from solution, if its molecular weight and cross-link density was sufficiently high. Indeed, when the copolymerization reaction of a 1.25 wt % 9:1 mixture of AA and BAA was carried out with meticulous exclusion of oxygen for at least 16 hours (Supplementary Information), selective removal of copolymer from solution was achieved by centrifugation and microfiltration.

Route X can be used to retrieve ssDNA from a sequestered 1,650 bp amplicon. After binding of the amplicon, 5 ml of X was loaded into a wide agarose gel well. Electroelution for 30 minutes removed unreacted dsDNA, primers, and other charged contaminants. Subsequently, X was retrieved from the well, dispersed in buffer solution, and heated shortly to 95° C. to dehybridize the DNA. Subsequently the polymer was centrifuged down, and the supernatant was filtered over a microfiltration membrane. The obtained filtrate contained the ssDNA product without dsDNA or primer contaminations.

Route L.

Route L was developed as alternative to Route X. Linear copolymer (L) was formed by copolymerization of 10-1000 ng/μL AA-labeled DNA in the presence of 5 wt % AA with 0.05 wt % A as an additive (FIG. 1). The solution was briefly purged with nitrogen gas to remove most oxygen. After incubation for 3 h, the copolymer mixture had an average molecular weight of ~1.2 MDa with a polydispersity index (PDI) of 1.27 (FIG. 2B). The exclusion of oxygen enabled large molecular weight and a smaller PDI of the copolymer, which was beneficial for subsequent separation steps. Due to the large molar excess of AA and A monomers, only a small fraction of copolymer chains contained a DNA strand. Remarkably, the addition of one volume of methanol (MeOH) to a suspension of polymer L selectively precipitated L while leaving free DNA (250-10,000 bp) in solution. In contrast, a linear polymer of 100% AA (not containing a small fraction of A) nonspecifically and quantitatively co-precipitates DNA. Therefore the 1% fraction of negatively charged monomer A in the polymer L recipe helped suppress undesired DNA co-precipitation. Excellent precipitation efficiency and selectively was achieved in both native and denaturing conditions. Precipitation efficiency and selectivity were also sensitive to the ionic strength of the solution; thus all precipitation steps were carried out at an ionic strength between 30 to 50 mM.

Figure 2D:
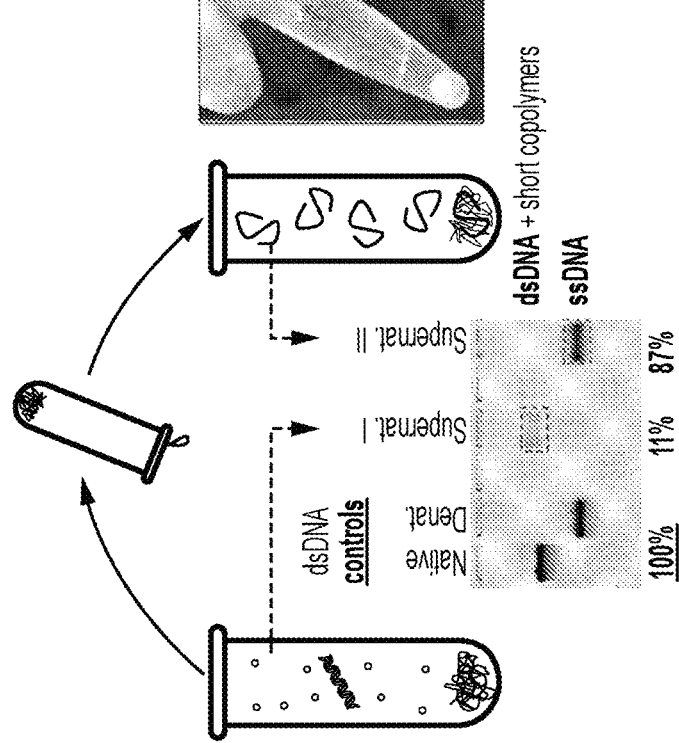

For isolation of ssDNA, L was first dispersed in TE buffer, then precipitated with MeOH and briefly centrifuged (Step I, FIGS. 2C-2C). Anchored dsDNA was dragged into the pellet by the precipitating polyacrylamide, whilst unreacted dsDNA, short copolymer chains, and other contaminants remained in the supernatant. In a second step, the polymer pellet was re-dispersed under basic denaturing conditions (36 mM NaOH, 0.36 mM EDTA) to release ssDNA from the copolymer. L was then precipitated with MeOH and removed from the released ssDNA by centrifugation (Step II, FIGS. 2C-2D). The clear supernatant, containing ssDNA in high yield with respect to the dsDNA amplicon, could then be recovered. In the final step, the released ssDNA was precipitated with isopropanol (iPrOH) and re-dispersed in TE buffer.

Product Yield and Quality.

AGE analysis of the supernatants from the first (native) and second (denaturing) steps showed that both supernatants contain together >95% of DNA, demonstrating that target loss due to co-precipitation or nonspecific binding to the copolymer is less than 5% (FIG. 2D). A small fraction of polymer L is too short to be efficiently precipitated in Step I. As this fraction of copolymer is discarded with the first supernatant, it does not contaminate the ssDNA product in the second supernatant.

Figure 2E:
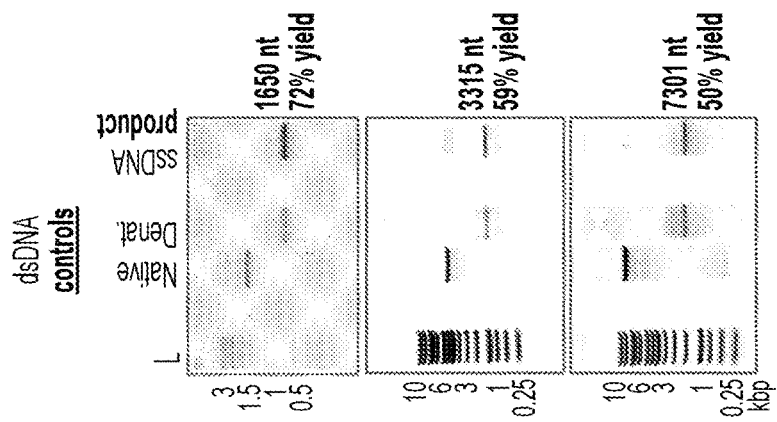

FIG. 2E shows the AGE analysis of three NPA-produced strands with 1650 nt (ss1650), 3315 nt (ss3315) and 7301 nt (ss7301) length. The dsDNA precursor in tris-borate-EDTA (TBE) or formamide-EDTA served as native and denatured controls, respectively. All three ssDNA products were obtained with good overall yield (50-70% with respect to the dsDNA precursor) and high purity. Product purity was also assessed by UV absorbance (Abs) measurements, showing ideal $Abs_{260}/Abs_{280}$ and $Abs_{260}/Abs_{230}$ ratios and no spectral signs of contamination.

To assess potential damage that the free radical polymerization can potentially cause DNA backbone breakage, supercoiled pBR322 plasmid (4,361 bp) was exposed to NPA polymerization conditions. No significant backbone breakage was detected, even when increasing the concentration of the radical initiator APS 10-fold. When nitrogen bubbling was omitted in the procedure, approximately 9% backbone lesions were observed in presence of 10-fold increased APS concentration. This finding indicates that under standard NPA conditions, DNA damage is negligible because (1) the concentration of radicals is low, and (2) exclusion of oxygen from the reaction prevents formation of reactive oxygen species, which could otherwise damage the DNA.

In direct comparison, the copolymerization step in Routes L and X binds long AA-tagged dsDNA selectively, and with efficiencies of 90% or higher. Both routes result in equally high product yields. Nonetheless, Route L was faster, easier, more scalable, and generated cleaner ssDNA product than did Route X.

DNA Origami Folded from NPA Produced ssDNA.

To demonstrate further downstream application of the produced ssDNA we folded several DNA origami objects from the two longer strands, ss3315 and ss7301 (FIGS. 3A-3C). A three-dimensional barrel structure was folded from ss3315. A rectangle and a 6-helix bundle were folded from ss7301. All folding reactions proceeded with near-quantitative conversion of the ssDNA precursor, as revealed by a band shift in AGE. DNA origami structures were directly observed by transmission electron microscopy (TEM), both in the crude folding mixture and when extracted from the major product band, thus confirming efficient folding of the respective structures (FIG. 3).

The experimentally measured diameter of the barrel was 27.3±0.9 nm (N=41), in good agreement with the anticipated value of ~27 nm. The measured lengths of rectangle and 6-helix bundle were 90.1±3.5 nm (N=54) and 405±11 nm (N=40), respectively. These values were also in excellent agreement with the anticipated values of ~90 nm and ~400 nm, respectively. Overall, these experiments generated the designed two- and three-dimensional structures with high fidelity and yield, comparable to M13-derived scaffold strands for DNA origami folding.

Example 2: Sequestration of Acrylamide-Labeled Oligonucleotides

Concentrations of APS, TEMED, and acrylamide (e.g., acrylamide-tagged dsDNA and acrylamide monomers) in polymerization reactions were adjusted to form linear or cross-linked copolymers with high molecular weight. In a total of 25 reactions, a single reaction yielded a partially gelled linear copolymer and a single reaction yielded a viscous linear copolymer (Table 1, Sample 13 and Sample 14). High molecular weight crosslinked copolymers were formed in overnight reactions comprising AA/BAA and low concentrations of APS and TEMED (Table 2).

TABLE 1

Polymerization of linear copolymers (LC).

| Sample # | C(APS) [wt %] | C(TEMED) [wt %] | C(acrylamide) [wt %] | fluid/viscous/gelled? | % volume retrieved | % mass sequestere |
|---|---|---|---|---|---|---|
| 1 | 0.05 | 0.1 | 1.5 | fluid | >98 | 44 |
| 2 | 0.1 | 0.1 | 1.5 | fluid | >98 | 53 |
| 3 | 0.2 | 0.1 | 1.5 | fluid | >98 | 51 |
| 4 | 0.5 | 0.1 | 1.5 | fluid | >98 | 47 |
| 5 | 0.05 | 0.5 | 1.5 | fluid | >98 | 42 |
| 6 | 0.1 | 0.5 | 1.5 | fluid | >98 | 43 |
| 7 | 0.2 | 0.5 | 1.5 | fluid | >98 | 44 |
| 8 | 0.5 | 0.5 | 1.5 | fluid | >98 | 50 |
| 9 | 0.05 | 2.5 | 1.5 | fluid | >98 | 12 |

TABLE 1-continued

Polymerization of linear copolymers (LC).

| Sample # | C(APS) [wt %] | C(TEMED) [wt %] | C(acrylamide) [wt %] | fluid/viscous/gelled? | % volume retrieved | % mass sequestere |
|---|---|---|---|---|---|---|
| 10 | 0.1 | 2.5 | 1.5 | fluid | >98 | 27 |
| 11 | 0.2 | 2.5 | 1.5 | fluid | >98 | 42 |
| 12 | 0.5 | 2.5 | 1.5 | fluid | >98 | 52 |
| 13 | 0.05 | 0.1 | 2 | partially gelled | 41 | 77 |
| 14 | 0.1 | 0.1 | 2 | viscous | 44 | 71 |
| 15 | 0.2 | 0.1 | 2 | fluid | >98 | 67 |
| 16 | 0.5 | 0.1 | 2 | fluid | >98 | 63 |
| 17 | 0.05 | 0.5 | 2 | fluid | >98 | 55 |
| 18 | 0.1 | 0.5 | 2 | fluid | >98 | 54 |
| 19 | 0.2 | 0.5 | 2 | fluid | >98 | 51 |
| 20 | 0.5 | 0.5 | 2 | fluid | >98 | 49 |
| 21 | 0.05 | 2.5 | 2 | fluid | >98 | 4 |
| 22 | 0.1 | 2.5 | 2 | fluid | >98 | 37 |
| 23 | 0.2 | 2.5 | 2 | fluid | >98 | 41 |
| 24 | 0.5 | 2.5 | 2 | fluid | >98 | 42 |
| 25 | 0 | 0 | 0 | fluid | >98 | 0 |

TABLE 2

Polymerization of high molecular weight crosslinked copolymer (HMWCC).

| mono-/bis-AA ratio | C(AA) [wt %] | | | | |
|---|---|---|---|---|---|
|  | 0.75 | 1 | 1.5 | 2 | 4 |
| 90:10 | #1 | #2 | #3 | — | — |
| 95:5 | — | #4 | #5 | — | — |
| 98:2 | — | #6 | #7 | #8 | — |
| 99:1 | — | #9 | #10 | #11 | #12 |
| 100:0 | — | — | #13 | #14 | #15 |

The efficiency of HMWCC polymerization and sequestration was examined using an acrylamide-labeled 41-nt ssDNA. HMWCC were polymerized with increasing mass ratios of AA/BAA in (e.g., AA/BAA ratios of 9:1, 19:1, 49:1, and 99:1) and removed from solution via filtration through a 0.45 mm cellulose acetate membrane. Sequestration efficiency and copolymer filtration efficiency were calculated from determinations of the oligonucleotide (oligo) mass.

Figure 8:
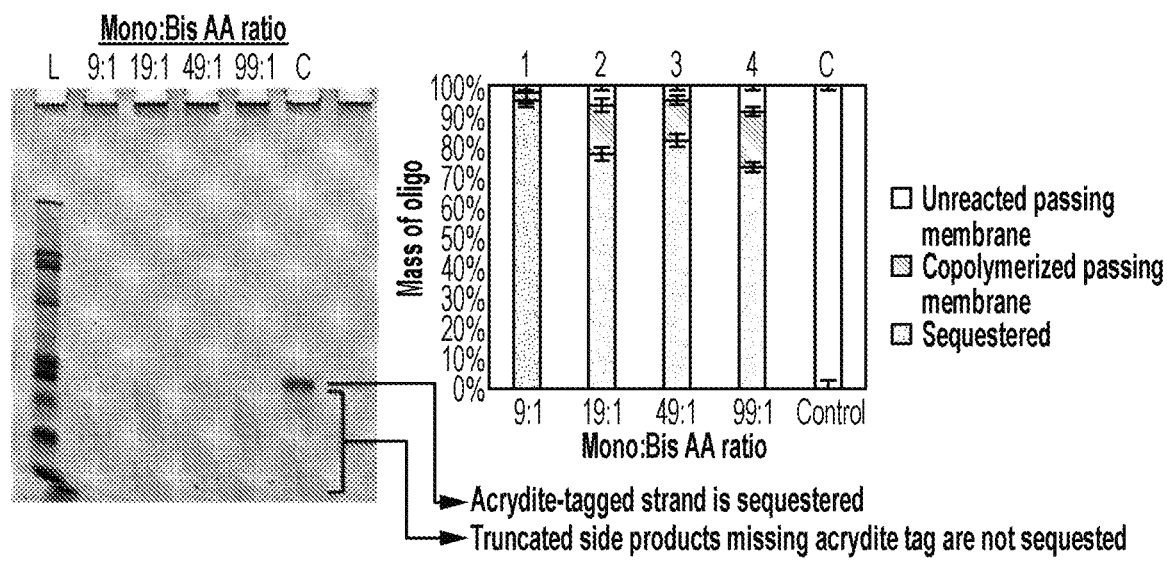
FIG. 8 shows a gel image (left) and graph (right) demonstrating sequestration of an acrylamide-labeled oligonucleotide strand via copolymerization with mixtures of acrylamide (AA) with bisacrylamide (BAA) in varying mass ratios. Left: polyacrylamide gel electrophoresis of the filtrates (C=unlabeled control strand). Right: Quantification of sequestration and copolymer filtration efficiency.

Polyacrylamide gel electrophoresis of filtrates showed that HMWCC formed in various mass ratios of AA/BAA were efficiently removed from solution via filtration (FIG. 8, left). In contrast, unlabeled truncated byproducts of the oligonucleotide synthesis and the unlabeled control strand were not sequestered, demonstrating the selectivity of the process (FIG. 8, left). Similar HMWCC copolymerization yields were observed for reactions comprising increasing mass ratios of AA/BAA (FIG. 8, right). HMWCC that formed in a 9:1 AA/BAA ratio was more efficiently removed from solution via filtration than HMWCC that formed at a 19:1, 49:1, or 99:1 AA/BAA ratio (FIG. 8, right). Thus, a low AA/BAA ratio may be used for efficient sequestration and separation of acrylamide-labeled dsDNA via HMWCC.

Figure 9:
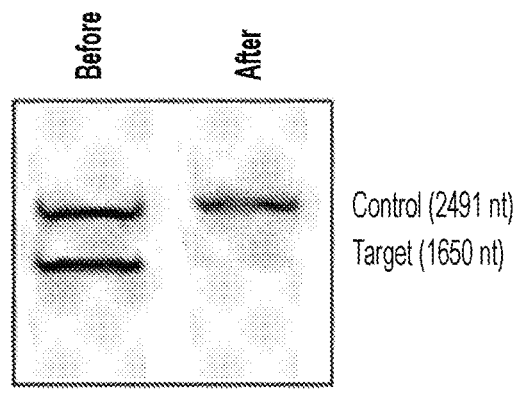
FIG. 9 shows a gel image demonstrating selective sequestration of an acrylamide-labeled target strand (1650 nucleotides) from an unlabeled control strand (2491 nucleotides).
Figure 10:
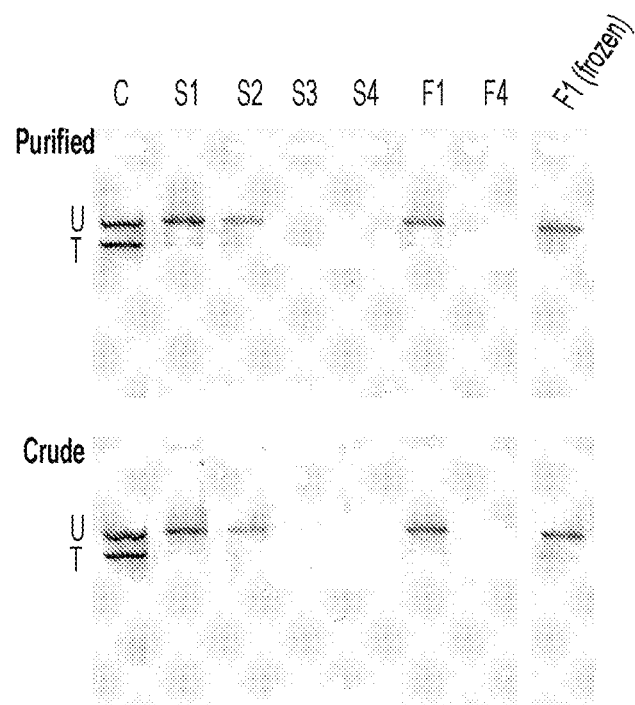
FIG. 10 shows a gel image demonstrating that purified PCR products and unpurified crude PCR products are efficiently sequestered.

Long PCR-amplified strands can also be efficiently and selectively sequestered by the disclosed method. An acrylamide-labeled PCR-amplified strand (1650 nt) was selectively sequestered from an unlabeled control strand (2491 nt) as shown by agarose gel electrophoresis (FIG. 9). The acrylamide-labeled strand was sequestered with 93% efficiency from the control strand. The longer control strand was not entrapped within the copolymer matrix, thereby demonstrating that the polymerization was selective toward the acrylamide-labeled strands. Similar sequestration efficiencies were observed for unpurified crude PCR products and purified PCR products (FIG. 10).

Example 3: Copolymer Purification

When high purity of the released ssDNA is desired, the copolymer can be conveniently purified from contaminations prior to release of the ssDNA. Contaminants may include unreacted dsDNA, excess primers, nucleotides, polymerase, or salts.

Selective precipitation: Both LC and HMWCC were selectively precipitated under native conditions (e.g., LC in TBE buffer) by addition of 2 or 3 volumes of methanol. The solution was decanted, and the purified copolymer was reconstituted (redispersed) in aqueous buffer. This purification method can be performed at any scale.

Figure 11:
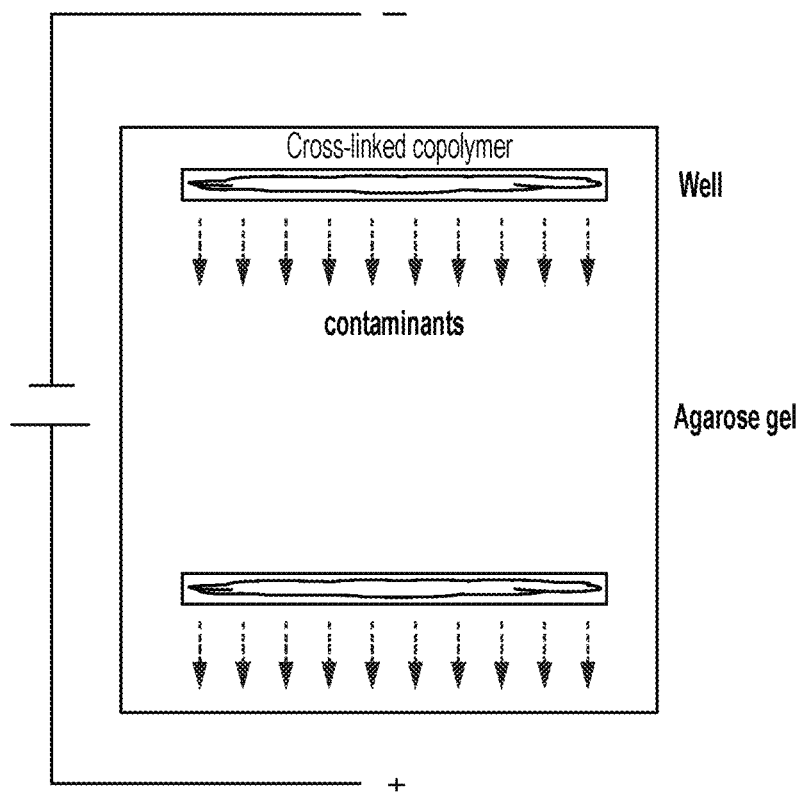
FIG. 11 shows a schematic representative of an optional purification of the high molecular weight cross-linked copolymer (HMWCC) via electroelution within an agarose gel. Total well loading capacity for a standard gel is 10 mL.

Electroelution: HMWCC can be purified using electroelution in an agarose gel (FIG. 11). HMWCC, loaded into wells in the gel, may be exposed to an electric current for 20 minutes, thereby eluting charged contaminants into the agarose gel. Subsequently, the purified HMWCC may be recovered from the well, and the agarose gel discarded. At least 10 mg of DNA can be purified using electroelution in a single agarose gel in 20 minutes.

Example 4: Separation and Single Strand Retrieval

Figure 12:
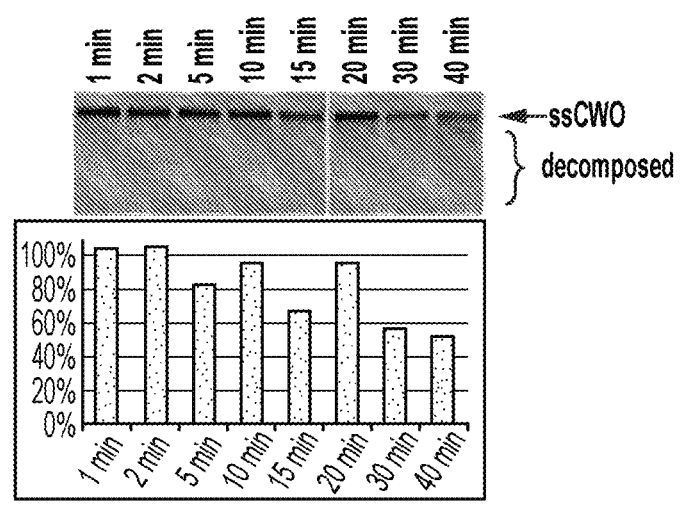
FIG. 12 shows a gel image demonstrating that dehybridization involving prolonged heating can lead to ssDNA decomposition.

Dehybridization of copolymerized dsDNA to produce ssDNA was achieved, for example, by dispersing LC or HMWCC in basic dehybridization solution (BDS, 100 mM NaOH, 1 mM EDTA) or formamide dehybridization buffer (FDB, 95% (v/v) formamide, 5 mM EDTA, pH 8.1). Dehybridization in BDS or FDB can be carried out at elevated temperatures to facilitate complete strand separation. LC or HMWCC as dehybridized in commonly used aqueous buffers (e.g., Tris-EDTA, TE) heated to 95° C. for 2 minutes. Prolonged heating should be avoided because it has been shown to cause significant ssDNA decomposition (FIG. 12).

The disclosure provides at least two methods (e.g., selective precipitation and size separation) for separating the released ssDNA from the copolymer.

Figure 13A:
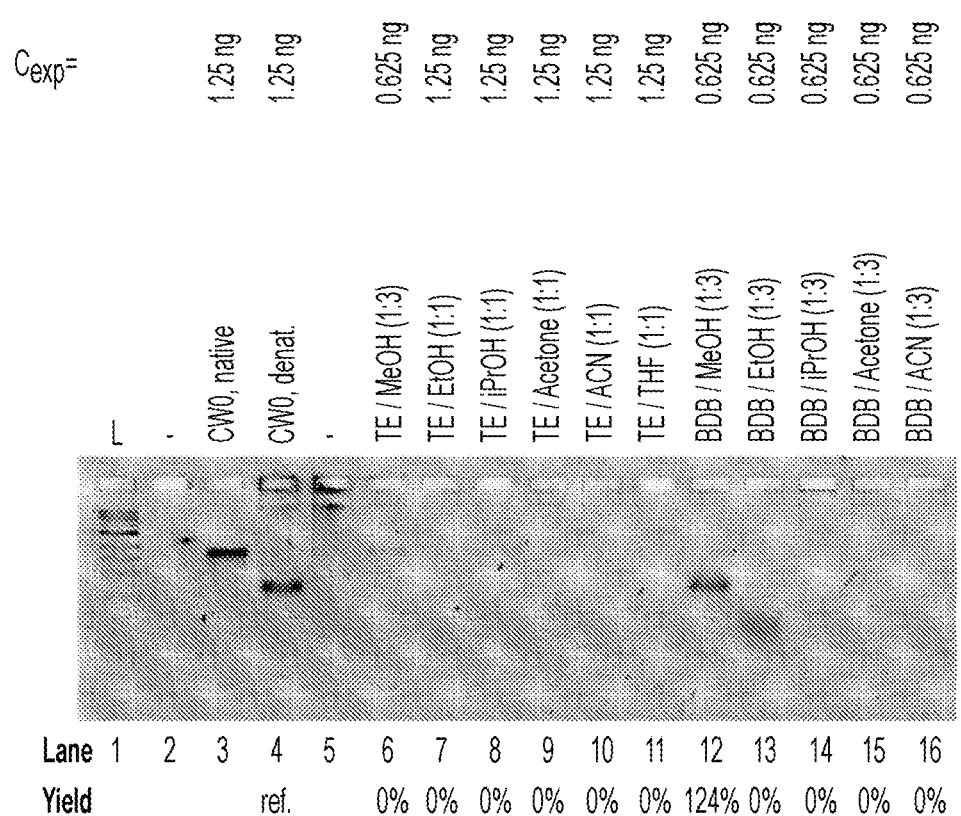
FIG. 13A-13B show images of selective precipitation of acrylamide/DNA copolymers under selected solvent mixtures. A 1650-nucleotide-long single-stranded DNA molecule (ssCW0) was retrieved with high purity and yield under native conditions in methanol and TE, or methanol and basic dehybridization buffer (BDB) (FIG. 10A). The ssDNA was retrieved with high purity and yield under denaturing conditions in methanol and formamide dehybridization buffer (FDB), or FDB and dimethylformamide (DMF) (FIG. 10B).
Figure 13B:
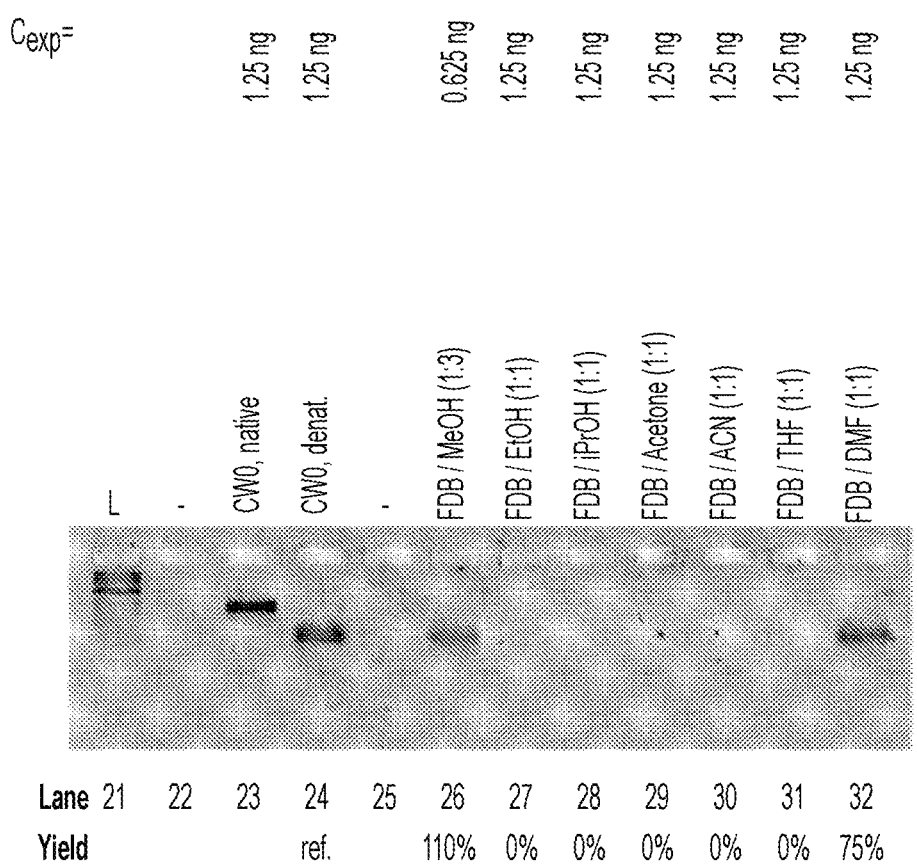
Figure 14:
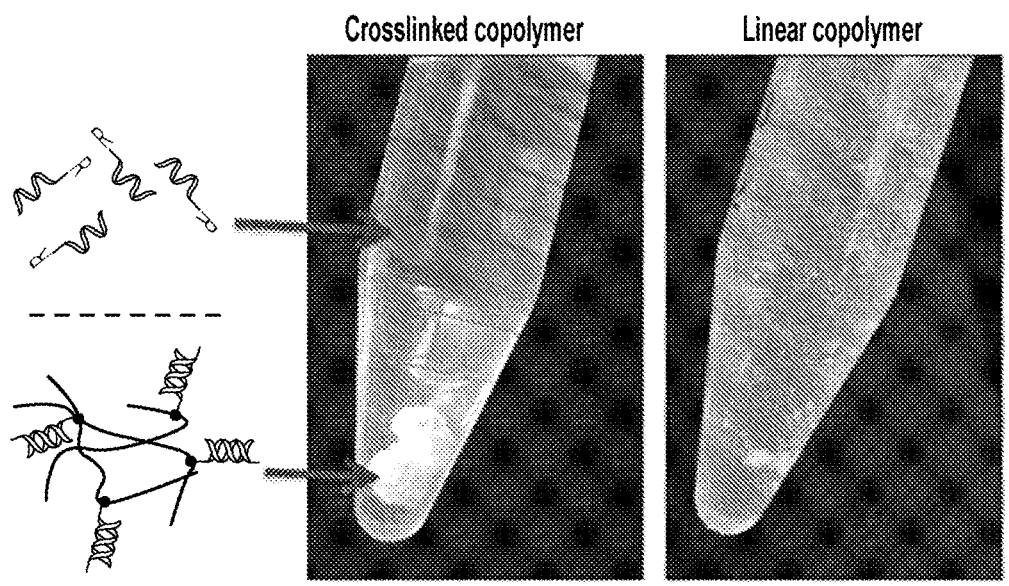
FIG. 14 shows images of selective precipitation of acrylamide/DNA copolymers under denaturing conditions. Left photograph: HMWCC precipitates as a single macroscopic particle. Right photograph: Precipitated linear copolymer (LC) particles.

Selective precipitation: LC or HMWCC was precipitated using methanol under native conditions or denaturing conditions (FIGS. 13A-13B). Several organic solvents precipitated both the copolymer and ssDNA (FIGS. 13A_13B). Although LC did not precipitate as a single particle, precipitated LC could be separated from solution comprising ssDNA using a benchtop centrifuge. Precipitation of HMWCC resulted in a single macroscopic particle that was directly separated from the solution with forceps or by decanting (FIG. 14). Selective precipitation is inexpensive, adaptable to large-scale ssDNA preparations, and efficiently separates ssDNA from LC or HMWCC.

Size separation: HMWCC can be removed from solution by inexpensive methods such as microfiltration[24] or centrifugation. Size separation can be performed in an aqueous buffer without the addition of an organic solvent that may interfere with subsequent experimentation. Exemplary microfiltration membranes are cellulosed acetate (CA) membranes or polyethersulfone (PES) membranes, which are inexpensive and do not absorb DNA. HMWCC separation using ultracentrifugation (e.g., 150000 g for 30 minutes) produced a voluminous HMWCC pellet that can be easily separated from solution.

Figure 15A:
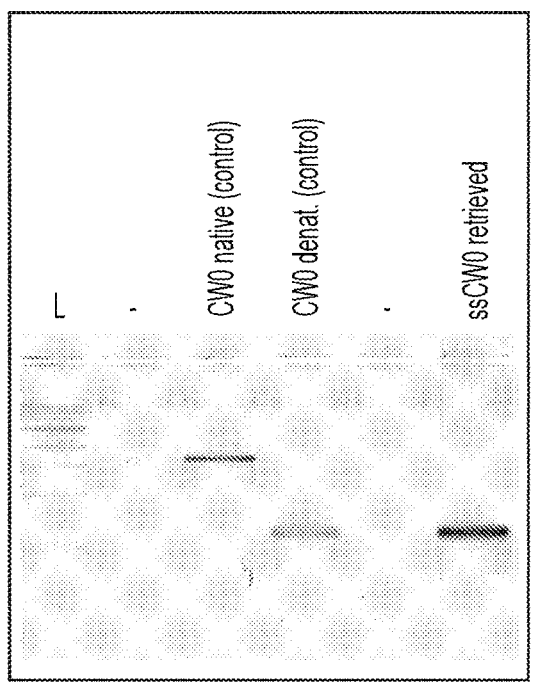
FIGS. 15A-15B show retrieval of two different 1650-nucleotide-long single-stranded DNA molecules (ssCW0 and ssCW1) with high purity and yield.
Figure 15B:
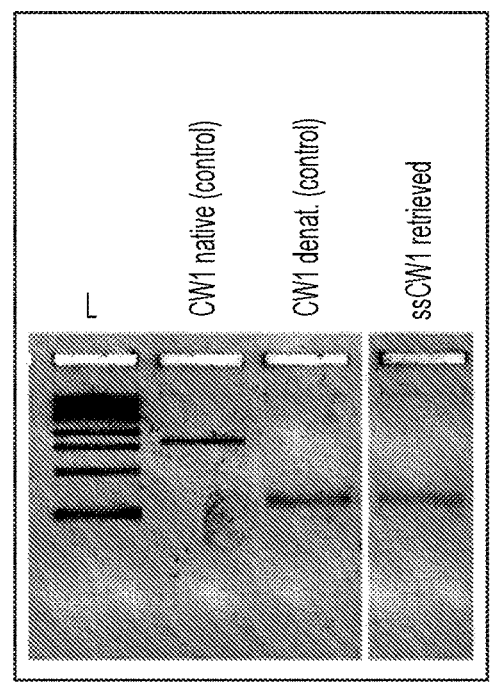
Figure 16:
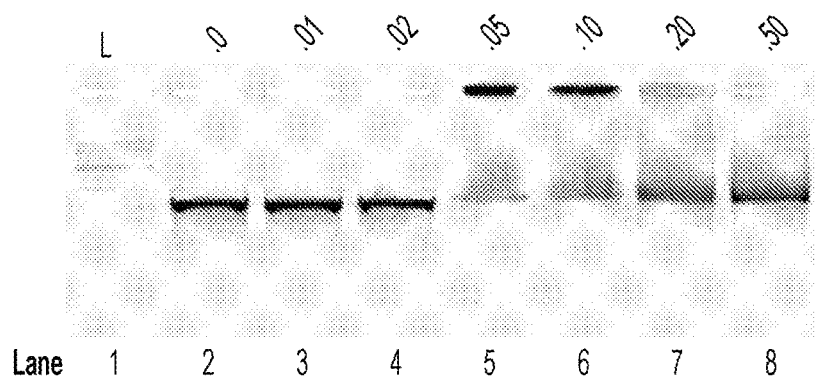
FIG. 16 shows a gel image demonstrating that oxygen can cause polymer chain growth to terminate at 0.01% (wt %) TEMED and 0.01% (wt %) APS, conditions in which polymers will form in solutions degassed with nitrogen.

The released ssDNA can be subjected to ethanol or isopropanol precipitation using standard procedures to obtain a dry sample that can be later dissolved in a desired buffer. For example, two 1650 nucleotide-long ssDNA molecules (CW0 and CW1) were released from LC or HMWCC with high purity and yield as shown by agarose gel electrophoresis (FIGS. 15A-15B). The overall yield of ssDNA recovery with respect to dsDNA precursor was approximately 70% for ssCW0 released from HMWCC (FIG. 12A) and ssCW1 released from LC (FIG. 12B).

Example 5: LC Polymerization and Production of ssDNA

Described below is an example of production of ssDNA using sequestration of LC formed from copolymerization of AA with acrylamide-labeled dsDNA.

In a 2000 µL reaction, components were be added to a septum-sealed glass vial in the following order $H_2O$, 1×TBE pH 8.15, 50 ng/µL acrylamide-labeled dsDNA, 5% (wt %) AA, 0.01% (wt %) TEMED, and 0.01% (wt %) APS. The solution was degassed with nitrogen for 10 minutes to remove the presence of oxygen, which causes polymer chain growth to terminate (FIG. 13). The glass vial was sealed and incubated on a shaker at 500 rpm for 2 hours. The solution turned highly viscous after incubation indicating the formation of LC.

Following dehybridization, LC was precipitated under native or denaturing conditions that selectively precipitate polyacrylamide while the release ssDNA remained in solution. The copolymerization reaction (1.5 mL) was diluted in 1×TE buffer pH 8.0 (13.5 mL) in a 50 mL Eppendorf tube. The tube was vortexed for 1 minute.

For precipitation under native conditions, the diluted copolymerization reaction (7.5 mL) was transferred into an Eppendorf tube and 2 or 3 volumes of MeOH (22.5 mL) was added to the tube and vortexed briefly to form a white precipitate. Reactions were incubated for 10 min and then centrifuged at 4000 g for 1 minute to obtain the supernatant comprising ssDNA.

For precipitation under denaturing conditions, the diluted copolymerization reaction (7.5 mL) was dispersed in BLB (7.5 mL) and incubated with shaking at 37° C. for at least 15 minutes. Once the material was completely dispersed, the solution was heated to 95° C. for 3 minutes. The solution was quickly cooled to room temperature and 2× or 3× volume (22.5 mL) of MeOH was added to each tube and vortexed briefly to form a white precipitate. Reactions were centrifuged at 4000 g for 1 minute to obtain the supernatant comprising ssDNA.

ssDNA was precipitated from the supernatant according to the following procedure. Supernatant was combined with 10 vol % NaOAc (3 mL), vortexed, and transferred to a 50 mL Falcon tube. Cold EtOH was added to each tube (2.5 vol, 27.5 mL). Tubes were vortexed and incubated for 2 hours at −20° C. The solution was centrifuged at 4000 g for 30 min at 4° C. and the supernatant was removed. To each supernatant, 70% EtOH (1 mL) was added and the solution was centrifuged at 4000 g for 10 min at 4° C. The supernatant was removed and pellets are allowed to air-dry for 30 minutes at room temperature. DNA pellets were resuspended in TE buffer and analyzed by agarose gel electrophoresis and absorbance. Resuspended DNA was stored at 4° C.

Example 6: HMWCC Polymerization and Production of ssDNA

Described below is an example of production of ssDNA using sequestration of HMWCC formed from copolymerization of AA/BAA with acrylamide-labeled DNA.

In a 2000 µL reaction, components were added to a septum-sealed glass vial in the following order $H_2O$, 1×TBE pH 8.15, 50 ng/µL acrylamide-labeled dsDNA, 9:1 AA/BA, 0.002% (wt %) TEMED, and 0.002% (wt %) APS. The solution was degassed with nitrogen for 30 minutes to remove the presence of oxygen, which causes polymer chain growth to terminate (FIG. 13). The glass vial was sealed and incubated in a desiccator for 20 hours. The solution turned into a soft gel indicating the formation of HMWCC.

HMWCC was also purified by electroelution. HMWCC was added to a well of a 1.2% agarose gel without stain. The gel was run for 20 minutes at 90V. The HMWCC was then transferred from the well into a tube and 1×TE buffer pH 9 was added to a total volume of 3 mL.

Dehybridization of the dsDNA was carried out by placing the tube into a 80° C. warm water bath. After the solution equilibrates in the warm bath for 5 minutes, boiling hot 1×TE buffer pH 9 was added to a total volume of 15 mL. The solution was vortexed for 20 seconds and then transferred to ice. The solution was centrifuged at 150000 g for 30 minutes at 4° C. The supernatant was filtered over a CA filter to obtain ~12.5 mL of filtrate comprising ssDNA.

ssDNA was precipitated from the supernatant according to the following procedure. Supernatant was combined with 10 vol % NaOAc (3 mL), vortexed, and transferred to a 50 mL Falcon tube. Cold EtOH was added to each tube (2.5 vol, 27.5 mL). Tubes were vortexed and incubated for 2 hours at −20° C. The solution was centrifuged at 5000 g for 30 min at 4° C. and the supernatant was removed. To each supernatant, 70% EtOH (1 mL) was added and the solution was centrifuged at 5000 g for 5 min at 4° C. The supernatant was removed and pellets were allowed to air-dry for 30 minutes at room temperature. DNA pellets were resuspended in TE buffer and analyzed by agarose gel electrophoresis and absorbance. Resuspended DNA was stored at 4° C.

Example 7: Kit for Sequestration of dsDNA and Release of ssDNA

The following kit may be used to isolate of ssDNA from a solution of acrydite-labeled dsDNA. The acrydite-labeled dsDNA is readily obtained by standard PCR amplification of the desired target molecule, using a regular forward primer and an acrydite-labeled reverse primer.

Components
1. 40 wt % acrylamide in TBE buffer (2.5×, 1 ml) in darkened, septum-sealed tube (4 ml volume)
2. TEMED in darkened vial (100%, liquid)
3. Tablets containing 1 mg APS
4. Long syringe needle for nitrogen purging
5. 50 ml centrifuge tubes
6. TE buffer (pH 8)
7. Methanol
8. Basic denaturing buffer (BDB): 0.1M NaOH+1 mM EDTA
9. NaOAc (3M, pH 5.25)
10. EtOH, 70%
11. EtOH, 100%

Additional Components
12. Acrydite-labeled dsDNA amplicon (up to 1 mg/ml concentration)
13. Nitrogen gas Protocol
Polymerization
Add 1 ml of the dsDNA sample to tube #1
Add 0.2 µL liquid #2
Add one tablet #3
Add septum cap but leave a half-rotation open
Insert needle (#4) through septum and gently bubble solution with $N_2$ for 10 minutes
Tightly close septum cap and directly retract and discard syringe
Incubate for 2 h while gently shaking
The solution should turn highly viscous MeOH Precipitation
After incubation, transfer solution to a 50 ml centrifuge tube (#5)
Add 10 ml solution #6 and vortex
Add 36 ml solution #7 and vortex
A precipitate should form immediately
Centrifuge at 4000 g for 1 min and discard supernatant
Re-disperse precipitate in 12 ml solution #8 by inverting at 37° C. for 15 min
Heat up solution in a water bath to 95° C. for 5 minutes
Cool down solution in an ice bath for 2 minutes
Add 36 ml MeOH and vortex
Spin down precipitate at 4000 g for 1 min and split supernatant into four 50 ml tubes EtOH Precipitation
Add to each tube 0.9 ml #9 followed by 25 ml #11
Vortex and incubate for 2 h −20° C.
Centrifuge at 4000 g for 30 min at 4° C.
Decant supernatant and add to each sample 1 mL solution #11
Centrifuge at 4000 g for 10 min at 4° C.
Remove supernatant
Air-dry pellets for 30 min at r.t.
Add to each pellet 250 µL TE buffer and shake for 10 min at 37° C.
Combine solutions
Store in Eppendorf tube at 4° C.

Example 8: Kit for Selective Sequestration of DNA-Labeled Target Systems

This solution contains a high molecular weight polymer (#1), which selectively sequesters any target system (e.g. DNA, protein) that is labeled with an oligonucleotide with the sequence CTTACACTGGTGTAAGCGCG (SEQ ID NO: 1). The polymer can be retained on a filter membrane. The resulting filtrate contains the original solution components without the target system. If required, the target system can be released from the polymer pellet by adding a release strand (#4), followed by separation from the polymer by filtration. 100 µL polymer solution can specifically bind up to 100 pmol of target systems.

Components
1. 1.5 ml Centrifuge tubes containing 100 µL of the HMWCC copolymer (1.25 wt %, 9:1 Acrylamide/Bisacrylamide) endowed with 1 µmol/L oligonucleotide handles with the sequence TAGCCAACAACGCGCTTACACCAGTGTAAG (SEQ ID NO: 2)
2. Centrifuge tubes
3. Cellulose acetate filters
4. Release strands with sequence CTTACACTGGTGTAAGCGCGTTGTTGGCTA (SEQ ID NO: 3) (0.1 µmol/L)

Protocol
Sequestration
Add up to 1.4 ml of the target solution to centrifuge tube #1
Invert solution for 30 minutes at 20 to 40° C.
Centrifuge tube at 25,000 g for 30 minutes
Decant centrifugate from pellet and filter through #3
The filtrate contains the original solution components without the target system
Target Retrieval (Optional)
Redisperse pellet in 1 ml buffer #4
Incubate for 30 minutes at 20 to 40° C.
Centrifuge tube at 25,000 g for 30 minutes
Decant centrifugate and filter through #3
The filtrate contains the target system

REFERENCES

1. Seeman, N. C. An Overview of Structural DNA Nanotechnology. *Mol. Biotechnol.* 37, 246-257 (2007).
2. Rothemund, P. W. K. Folding DNA to create nanoscale shapes and patterns. *Nature* 440, 297-302 (2006).
3. Andersen, E. S. et al. Self-assembly of a nanoscale DNA box with a controllable lid. *Nature* 459, 73-76 (2009).
4. Douglas, S. M., Bachelet, I. & Church, G. M. A Logic-Gated Nanorobot for Targeted Transport of Molecular Payloads. *Science* 335, 831-834 (2012).
5. Zhao, Y.-X. et al. DNA Origami Delivery System for Cancer Therapy with Tunable Release Properties. *ACS Nano* 6, 8684-8691 (2012).
6. Perrault, S. D. & Shih, W. M. Virus-Inspired Membrane Encapsulation of DNA Nanostructures To Achieve In Vivo Stability. *ACS Nano* 8, 5132-5140 (2014).
7. Kuzyk, A. et al. DNA-based self-assembly of chiral plasmonic nanostructures with tailored optical response. *Nature* 483, 311-314 (2012).
8. Amir, Y. et al. Universal computing by DNA origami robots in a living animal. *Nat. Nanotechnol.* 9, 353-357 (2014).
9. Douglas, S. M., Chou, J. J. & Shih, W. M. DNA-nanotube-induced alignment of membrane proteins for NMR structure determination. *Proc. Natl. Acad. Sci.* 104, 6644-6648 (2007).
10. Douglas, S. M. et al. Self-assembly of DNA into nanoscale three-dimensional shapes. *Nature* 459, 414-418 (2009).

11. Pinheiro, A. V., Han, D., Shih, W. M. & Yan, H. Challenges and opportunities for structural DNA nanotechnology. *Nat. Nanotechnol.* 6, 763-772 (2011).
12. Kosuri, S. & Church, G. M. Large-scale de novo DNA synthesis: technologies and applications. *Nat. Methods* 11, 499-507 (2014).
13. Svobodová, M., Pinto, A., Nadal, P. & Sullivan, C. K. O. Comparison of different methods for generation of single-stranded DNA for SELEX processes. *Anal. Bioanal. Chem.* 404, 835-842 (2012).
14. Kenney, M., Ray, S. & Boles, T. C. Mutation typing using electrophoresis and gel-immobilized Acrydite probes. *BioTechniques* 25, 516-521 (1998).
15. Rehman, F. N. et al. Immobilization of acrylamide-modified oligonucleotides by co-polymerization. *Nucleic Acids Res.* 27, 649-655 (1999).
16. Vasiliskov, A. V. et al. Fabrication of microarray of gel-immobilized compounds on a chip by copolymerization. *BioTechniques* 27, 592-594, 596-598, 600 passim (1999).
17. Mitra, R. D., Shendure, J., Olejnik, J., Edyta-Krzymanska-Olejnik, null & Church, G. M. Fluorescent in situ sequencing on polymerase colonies. *Anal. Biochem.* 320, 55-65 (2003).
18. Liu, J. Oligonucleotide-functionalized hydrogels as stimuli responsive materials and biosensors. *Soft Matter* 7, 6757-6767 (2011).
19. Xiong, X. et al. Responsive DNA-Based Hydrogels and Their Applications. *Macromol. Rapid Commun.* 34, 1271-1283 (2013).
20. Wei, B., Cheng, I., Luo, K. Q. & Mi, Y. Capture and Release of Protein by a Reversible DNA-Induced Sol-Gel Transition System. *Angew. Chem. Int. Ed.* 47, 331-333 (2008).
21. Dave, N., Chan, M. Y., Huang, P.-J. J., Smith, B. D. & Liu, J. Regenerable DNA-Functionalized Hydrogels for Ultrasensitive, Instrument-Free Mercury(II) Detection and Removal in Water. *J. Am. Chem. Soc.* 132, 12668-12673 (2010).
22. He, X., Wei, B. & Mi, Y. Aptamer based reversible DNA induced hydrogel system for molecular recognition and separation. *Chem. Commun.* 46, 6308-6310 (2010).
23. Liedl, T., Dietz, H., Yurke, B. & Simmel, F. Controlled Trapping and Release of Quantum Dots in a DNA-Switchable Hydrogel. *Small* 3, 1688-1693 (2007).
24. Krieg, E., Weissman, H., Shirman, E., Shimoni, E. & Rybtchinski, B. A recyclable supramolecular membrane for size-selective separation of nanoparticles. *Nat. Nanotechnol.* 6, 141-146 (2011).
25. Beaucage, S. L. & Caruthers, M. H. Deoxynucleoside phosphoramidites-A new class of key intermediates for deoxypolynucleotide synthesis. *Tetrahedron Lett.* 22, 1859-1862 (1981).
26. Kick, B., Praetorius, F., Dietz, H. & Weuster-Botz, D. Efficient Production of Single-Stranded Phage DNA as Scaffolds for DNA Origami. *Nano Lett.* (2015). doi: 10.1021/acs.nanolett.5b01461
27. Bowman, B. H. & Palumbi, S. R. in (ed. Enzymology, B.-M. in) 224, 399-406 (Academic Press, 1993).
28. Pound, E., Ashton, J. R., Becerril, H. A. & Woolley, A. T. Polymerase Chain Reaction Based Scaffold Preparation for the Production of Thin, Branched DNA Origami Nanostructures of Arbitrary Sizes. *Nano Lett.* 9, 4302-4305 (2009).
29. Gyllensten, U. B. & Erlich, H. A. Generation of single-stranded DNA by the polymerase chain reaction and its application to direct sequencing of the HLA-DQA locus. *Proc. Natl. Acad. Sci. U.S.A.* 85, 7652-7656 (1988).
30. Remi Veneziano et al. Designer nanoscale DNA assemblies programmed from the top down. *Science* aaf4388 (2016). doi:10.1126/science.aaf4388
31. Hannon, K. et al. Synthesis of PCR-Derived, Single-Stranded DNA Probes Suitable for in Situ Hybridization. *Anal. Biochem.* 212, 421-427 (1993).
32. Kujau, M. J. & Wolfl, S. Efficient preparation of single-stranded DNA for in vitro selection. *Mol. Biotechnol.* 7, 333-335 (1997).
33. Fire, A. & Xu, S. Q. Rolling replication of short DNA circles. *Proc. Natl. Acad. Sci.* 92, 4641-4645 (1995).
34. Walker, G. T., Little, M. C., Nadeau, J. G. & Shank, D. D. Isothermal in vitro amplification of DNA by a restriction enzyme/DNA polymerase system. *Proc. Natl. Acad. Sci. U.S.A* 89, 392-396 (1992).
35. Joneja, A. & Huang, X. Linear nicking endonuclease-mediated strand-displacement DNA amplification. *Anal. Biochem.* 414, 58-69 (2011).
36. Chandra, M., Sachdeva, A. & Silverman, S. K. DNA-catalyzed sequence-specific hydrolysis of DNA. *Nat. Chem. Biol.* 5, 718-720 (2009).
37. Gu, H., Furukawa, K., Weinberg, Z., Berenson, D. F. & Breaker, R. R. Small, Highly Active DNAs That Hydrolyze DNA. *J. Am. Chem. Soc.* 135, 9121-9129 (2013).
38. Hermanson, G. T. *Bioconjugate Techniques, Third Edition*. (Academic Press, 2013).

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing single-stranded deoxyribonucleic acid (ssDNA), comprising:
   (a) combining in solution acrylamide-labeled double-stranded deoxyribonucleic acid (dsDNA) and acrylamide (AA) monomers to form copolymer-linked dsDNA in solution;
   (b) dehybridizing the copolymer-linked dsDNA in solution to produce free ssDNA and DNA-containing copolymer; and
   (c) separating the free ssDNA from the solution of (b).

2. The method of claim 1, wherein separating the free ssDNA from the solution of (b) comprises adding methanol to the solution of (b) to selectively precipitate the DNA-containing copolymer.

3. The method of claim 1, wherein the length of the dsDNA is 100-10,000 nucleotide base pairs.

4. The method of claim 1, wherein the concentration of acrylamide monomers in the solution is 10-100 mg/ml.

5. The method of claim 1, wherein the concentration of acrylamide-labeled dsDNA in the solution is 0.01-10 mg/ml.

6. The method of claim 1, wherein the solution comprises ammonium persulfate (APS) and tetramethylethylenediamine (TEMED).

7. The method of claim 6, wherein the solution comprises ammonium persulfate at a concentration of 0.01 wt %-0.05 wt % and/or wherein solution comprises TEMED at a concentration of 0.01 wt %-0.05 wt %.

8. The method of claim 1, wherein the solution further comprises acrylate (A).

9. The method of claim 8, wherein the ratio of AA:A is 50:1 to 200:1.

10. The method of claim 8, wherein the copolymer-linked dsDNA comprises a linear copolymer.

11. The method of claim 1, wherein the solution comprises ammonium persulfate at a concentration of 0.0005 wt %-0.002 wt % and/or tetramethylethylenediamine (TMED) at a concentration of 0.0005 wt %-0.002 wt %.

12. The method of claim 1, wherein the solution further comprises a crosslinking agent.

13. The method of claim 12, wherein the crosslinking agent comprises bisacrylamide (BAA), piperazine diacrylamide, N,N'-Hexamethylenebis(methacrylamide), N,N'-ethylenebis(acrylamide), or combinations thereof.

14. The method of claim 13, wherein the BAA is N,N-methylenebisacrylamide.

15. The method of claim 13, wherein the ratio of AA:BAA in the solution is 9:1 to 1:1.

16. The method of claim 12, wherein the copolymer-linked dsDNA comprises a crosslinked copolymer.

17. The method of claim 1, wherein the copolymer-linked dsDNA comprises at least 80% of the acrylamide-labeled dsDNA from the solution.

18. The method of claim 1, further comprising incubating the solution of (a) for 1-3 hours.

19. The method of claim 1, wherein the dehybridizing of (b) comprises combining the copolymer-linked dsDNA with an aqueous buffer comprising (i) sodium hydroxide and ethylenediaminetetraacetic acid (EDTA); (ii) formamide and EDTA; or (iii) Tris-EDTA.

20. The method of claim 16, wherein the crosslinked copolymer has a molecular weight of at least 1000 kDa.

21. The method of claim 16, wherein the separating comprises passing the solution of (b) over a microfiltration membrane to remove the crosslinked DNA-containing copolymer.

22. The method of claim 16, wherein the separating comprises subjecting the solution of (b) to centrifugation to remove the crosslinked DNA-containing copolymer.

* * * * *

UNITED STATES PATENT AND TRADEMARK OFFICE
CERTIFICATE OF CORRECTION

| | | |
|---|---|---|
| PATENT NO. | : 11,767,523 B2 | |
| APPLICATION NO. | : 16/332674 | |
| DATED | : September 26, 2023 | |
| INVENTOR(S) | : Elisha Krieg et al. | |

It is certified that error appears in the above-identified patent and that said Letters Patent is hereby corrected as shown below:

In the Claims

In Claim 11, Column 26, Line 30, "TMED" should read --TEMED--.

In Claim 14, Column 26, Line 38, "N,N- methylenebisacrylamide" should read --N,N´- methylenebisacrylamide--.

Signed and Sealed this
Tenth Day of September, 2024

Katherine Kelly Vidal
*Director of the United States Patent and Trademark Office*